US011498943B2

(12) United States Patent
Kapurniotu et al.

(10) Patent No.: US 11,498,943 B2
(45) Date of Patent: Nov. 15, 2022

(54) AMYLOID INHIBITORY PEPTIDES

(71) Applicant: TECHNISCHE UNIVERSITÄT MÜNCHEN, Munich (DE)

(72) Inventors: Aphrodite Kapurniotu, Munich (DE); Anna Spanopoulou, Munich (DE); Luzia Heidrich, Bonn (DE); Jürgen Bernhagen, Munich (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 0 days.

(21) Appl. No.: 17/048,870

(22) PCT Filed: Jun. 6, 2019

(86) PCT No.: PCT/EP2019/064793
§ 371 (c)(1),
(2) Date: Oct. 19, 2020

(87) PCT Pub. No.: WO2019/234157
PCT Pub. Date: Dec. 12, 2019

(65) Prior Publication Data
US 2021/0340180 A1 Nov. 4, 2021

(30) Foreign Application Priority Data
Jun. 7, 2018 (EP) .................... 18176609

(51) Int. Cl.
*C07K 7/08* (2006.01)
*A61K 38/00* (2006.01)
(52) U.S. Cl.
CPC .............. *C07K 7/08* (2013.01); *A61K 38/00* (2013.01)
(58) Field of Classification Search
None
See application file for complete search history.

(56) References Cited

U.S. PATENT DOCUMENTS

2010/0204085 A1 8/2010 Eisenberg et al.

OTHER PUBLICATIONS

Miloš Erak, et al Peptide chemistry toolbox—Transforming natural peptides into peptide therapeutics, Bioorganic & Medicinal Chemistry, vol. 26, Issue 10, Jun. 1, 2018, pp. 2759-2765 (Year: 2018).*
Luo, Jinghui, et al., "Cyclic Peptides as Inhibitors of Amyloid Fibrillation", Chemistry—A European Journal, vol. 20, No. 9, Feb. 24, 2014, pp. 2410-2419.
Pathuri, Gopal, et al., "Radiosynthesis and In Vivo Evaluation of a F-18-Laveled Pancreatic Islet Amyloid Inihibitor", Journal of Labelled Compounds and Radiopharmaceuticals, vol. 53, No. 4, Jan. 2010, pp. 186-191.
Richman, Michal, et al., "In Vitro and Mechanistic Studies of an Antiamyloidogenic Self-Assembled Cyclic D,L-α-Peptide Architecture", JACS, vol. 135, Jan. 29, 2013, pp. 3474-3484.
Sellin, Daniel, et al., "Suppression of IAPP Fibrillation at Anionic Lipid Membranes via IAPP-Derived Amyloid Inhibitors and Insulin", Biophysical Chemistry, vol. 150, Aug. 2010, pp. 73-79.

* cited by examiner

*Primary Examiner* — Thomas S Heard
(74) *Attorney, Agent, or Firm* — Saliwanchik, Lloyd & Eisenchenk

(57) ABSTRACT

The present invention relates to peptides, in particular amyloid inhibitory peptides, and to pharmaceutical compositions comprising such peptides. Furthermore, the present invention relates to such peptides, in particular such amyloid inhibitory peptides, for use in methods of treating or diagnosing neurodegenerative diseases such as Alzheimer's disease, or for use in a method of treating or diagnosing type 2 diabetes. Furthermore, the present invention also relates to a kit for the in-vitro or in-vivo detection and, optionally, quantification of amyloidogenic polypeptides, amyloid fibrils or amyloid aggregates, and/or for the diagnosis of Alzheimer's disease or type 2 diabetes in a patient.

14 Claims, 6 Drawing Sheets

Figure 1:
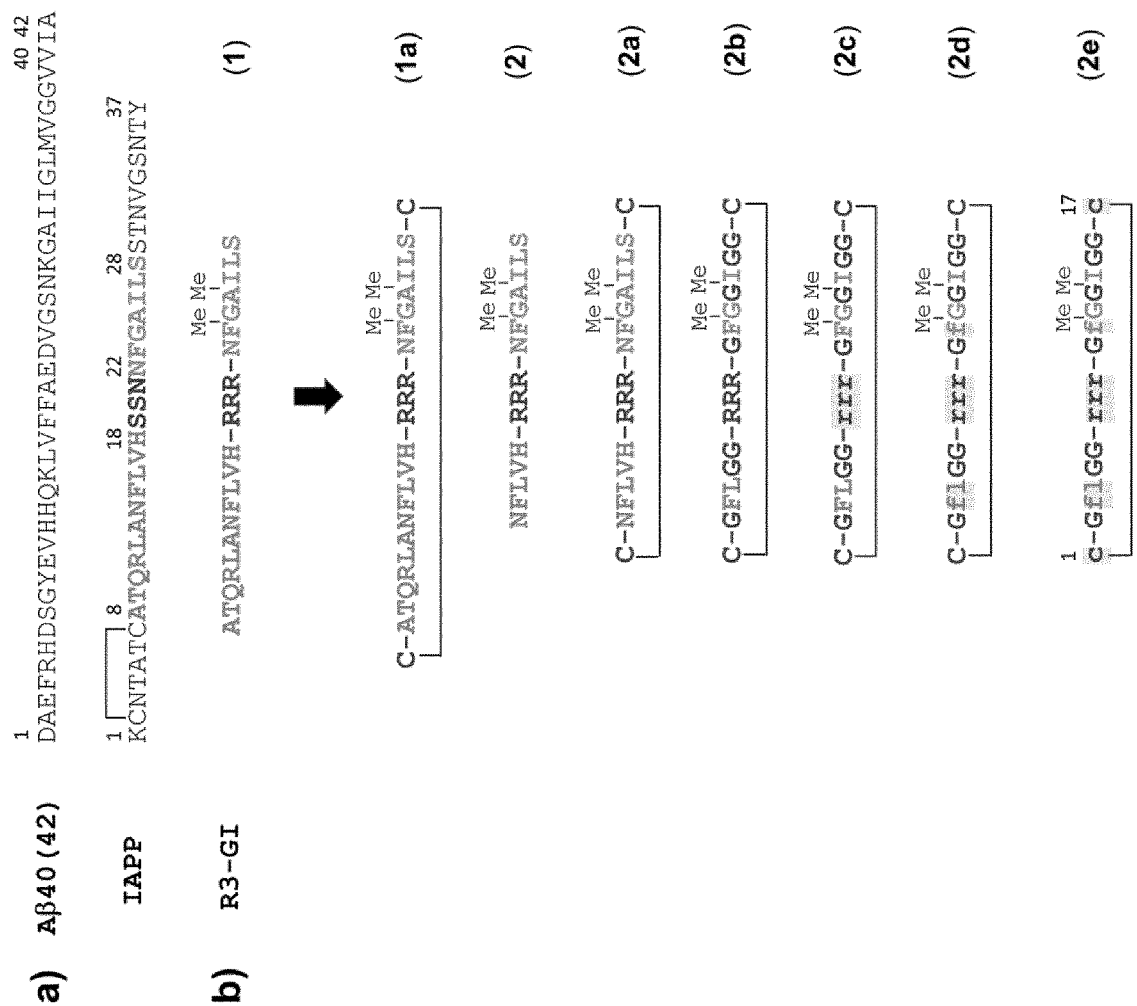

Specification includes a Sequence Listing.

SEQUENCE LISTING

<160> NUMBER OF SEQ ID NOS: 21

<210> SEQ ID NO 1
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: covalent bond between position 1 and 17
<220> FEATURE:
<221> NAME/KEY: VARIANT
<222> LOCATION: 1,17

```
<223> OTHER INFORMATION: selected from the following pairs: Cys/Cys,
      Asp/Lys, Asp/ornithine, Asp/2,4-diaminobutyric acid,
      Asp/2,3-diaminopropionic acid, Glu/Lys, Glu/ornithine,
      Glu/2,4-diaminobutyric acid, Glu/2,3-diaminopropionic acid;
<220> FEATURE:
<221> NAME/KEY: VARIANT
<222> LOCATION: 2,5,6,10,13,15,16
<223> OTHER INFORMATION: independently selected from glycine,
      asparagine, valine, histidine, leucine, serine, alanine, and
      threonine;
<220> FEATURE:
<221> NAME/KEY: VARIANT
<222> LOCATION: 7,8,9
<223> OTHER INFORMATION: independently selected from arginine,
      homoarginine, citrulline, ornithine, lysine, and norleucine;

<400> SEQUENCE: 1

Xaa Xaa Phe Leu Xaa Xaa Xaa Xaa Xaa Xaa Phe Gly Xaa Ile Xaa Xaa
1               5                   10                  15

Xaa

<210> SEQ ID NO 2
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: covalent bond between position 1 and 17
<220> FEATURE:
<221> NAME/KEY: VARIANT
<222> LOCATION: 1,17
<223> OTHER INFORMATION: selected from the following pairs: Cys/Cys,
      Asp/Lys, Asp/ornithine, Asp/2,4-diaminobutyric acid,
      Asp/2,3-diaminopropionic acid, Glu/Lys, Glu/ornithine,
      Glu/2,4-diaminobutyric acid, Glu/2,3-diaminopropionic acid
<220> FEATURE:
<221> NAME/KEY: VARIANT
<222> LOCATION: 2,5,6,10,13,15,16
<223> OTHER INFORMATION: independently selected from glycine,
      asparagine, valine, histidine, leucine, serine, alanine, and
      threonine
<220> FEATURE:
<221> NAME/KEY: VARIANT
<222> LOCATION: 7,8,9
<223> OTHER INFORMATION: independently selected from arginine,
      homoarginine, citrulline, ornithine, lysine, and norleucine
<220> FEATURE:
<221> NAME/KEY: MOD_RES
<222> LOCATION: 12,14
<223> OTHER INFORMATION: N-Methylation

<400> SEQUENCE: 2

Xaa Xaa Phe Leu Xaa Xaa Xaa Xaa Xaa Xaa Phe Gly Xaa Ile Xaa Xaa
1               5                   10                  15

Xaa

<210> SEQ ID NO 3
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: DISULFID
<222> LOCATION: 1,17
<223> OTHER INFORMATION: disulfide bond from position 1 to position 17
<220> FEATURE:
<221> NAME/KEY: VARIANT
<222> LOCATION: 2,5,6,10,13,15,16
<223> OTHER INFORMATION: independently selected from glycine,
``` asparagine, valine, histidine, leucine, serine, alanine, and
threonine
<220> FEATURE:
<221> NAME/KEY: MOD_RES
<222> LOCATION: 12,14
<223> OTHER INFORMATION: N-Methylation

<400> SEQUENCE: 3

Cys Xaa Phe Leu Xaa Xaa Arg Arg Arg Xaa Phe Gly Xaa Ile Xaa Xaa
1               5                   10                  15

Cys

<210> SEQ ID NO 4
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: DISULFID
<222> LOCATION: 1,17
<223> OTHER INFORMATION: disulfide bond from position 1 to position 17
<220> FEATURE:
<221> NAME/KEY: VARIANT
<222> LOCATION: 2,5,6,10,13,15,16
<223> OTHER INFORMATION: independently selected from glycine,
    asparagine, valine, histidine, leucine, serine, alanine, and
    threonine

<400> SEQUENCE: 4

Cys Xaa Phe Leu Xaa Xaa Arg Arg Arg Xaa Phe Gly Xaa Ile Xaa Xaa
1               5                   10                  15

Cys

<210> SEQ ID NO 5
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: disulfide bond from position 1 to position 17
<220> FEATURE:
<221> NAME/KEY: MOD_RES
<222> LOCATION: 12,14
<223> OTHER INFORMATION: N-Methylation

<400> SEQUENCE: 5

Cys Asn Phe Leu Val His Arg Arg Arg Asn Phe Gly Ala Ile Leu Ser
1               5                   10                  15

Cys

<210> SEQ ID NO 6
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: disulfide bond from position 1 to position 17
<220> FEATURE:
<221> NAME/KEY: MOD_RES
<222> LOCATION: 12,14
<223> OTHER INFORMATION: N-Methylation

<400> SEQUENCE: 6

Cys Gly Phe Leu Gly Gly Arg Arg Arg Gly Phe Gly Gly Ile Gly Gly
1               5                   10                  15

Cys

<210> SEQ ID NO 7
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: disulfide bond from position 1 to position 17
<220> FEATURE:
<221> NAME/KEY: SITE
<222> LOCATION: 7,8,9
<223> OTHER INFORMATION: D-amino acid residue
<220> FEATURE:
<221> NAME/KEY: MOD_RES
<222> LOCATION: 12,14
<223> OTHER INFORMATION: N-Methylation

<400> SEQUENCE: 7

Cys Gly Phe Leu Gly Gly Arg Arg Arg Gly Phe Gly Gly Ile Gly Gly
1               5                   10                  15

Cys

<210> SEQ ID NO 8
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: disulfide bond from position 1 to position 17
<220> FEATURE:
<221> NAME/KEY: SITE
<222> LOCATION: 3,4,7,8,9,11
<223> OTHER INFORMATION: D-amino acid residue
<220> FEATURE:
<221> NAME/KEY: MOD_RES
<222> LOCATION: 12,14
<223> OTHER INFORMATION: N-Methylation

<400> SEQUENCE: 8

Cys Gly Phe Leu Gly Gly Arg Arg Arg Gly Phe Gly Gly Ile Gly Gly
1               5                   10                  15

Cys

<210> SEQ ID NO 9
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,3,4,7,8,9,11,17
<223> OTHER INFORMATION: D-amino acid residue
<220> FEATURE:
<221> NAME/KEY: SITE
<222> LOCATION: 1,17
<223> OTHER INFORMATION: disulfide bond from position 1 to position 17
<220> FEATURE:
<221> NAME/KEY: MOD_RES
<222> LOCATION: 12,14
<223> OTHER INFORMATION: N-Methylation

<400> SEQUENCE: 9

Cys Gly Phe Leu Gly Gly Arg Arg Arg Gly Phe Gly Gly Ile Gly Gly
1               5                   10                  15
Cys

<210> SEQ ID NO 10
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: disulfide bond from position 1 to position 17

<400> SEQUENCE: 10

Cys Asn Phe Leu Val His Arg Arg Arg Asn Phe Gly Ala Ile Leu Ser
1               5                   10                  15
Cys

<210> SEQ ID NO 11
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: disulfide bond from position 1 to position 17

<400> SEQUENCE: 11

Cys Gly Phe Leu Gly Gly Arg Arg Arg Gly Phe Gly Gly Ile Gly Gly
1               5                   10                  15
Cys

<210> SEQ ID NO 12
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17
<223> OTHER INFORMATION: disulfide bond from position 1 to position 17
<220> FEATURE:
<221> NAME/KEY: SITE
<222> LOCATION: 7,8,9
<223> OTHER INFORMATION: D-amino acid residue

<400> SEQUENCE: 12

Cys Gly Phe Leu Gly Gly Arg Arg Arg Gly Phe Gly Gly Ile Gly Gly
1               5                   10                  15
Cys

<210> SEQ ID NO 13
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,17

```
<223> OTHER INFORMATION: disulfide bond from position 1 to position 17
<220> FEATURE:
<221> NAME/KEY: SITE
<222> LOCATION: 3,4,7,8,9,11
<223> OTHER INFORMATION: D-amino acid residue

<400> SEQUENCE: 13

Cys Gly Phe Leu Gly Gly Arg Arg Arg Gly Phe Gly Gly Ile Gly Gly
1               5                   10                  15

Cys

<210> SEQ ID NO 14
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,3,4,7,8,9,11,17
<223> OTHER INFORMATION: D-amino acid residue
<220> FEATURE:
<221> NAME/KEY: SITE
<222> LOCATION: 1,17
<223> OTHER INFORMATION: disulfide bond from position 1 to position 17

<400> SEQUENCE: 14

Cys Gly Phe Leu Gly Gly Arg Arg Arg Gly Phe Gly Gly Ile Gly Gly
1               5                   10                  15

Cys

<210> SEQ ID NO 15
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: MOD_RES
<222> LOCATION: 11,13
<223> OTHER INFORMATION: N-Methylation

<400> SEQUENCE: 15

Asn Phe Leu Val His Arg Arg Arg Asn Phe Gly Ala Ile Leu Ser
1               5                   10                  15

<210> SEQ ID NO 16
<211> LENGTH: 42
<212> TYPE: PRT
<213> ORGANISM: Homo sapiens
<220> FEATURE:
<221> NAME/KEY: MISC_FEATURE
<222> LOCATION: (1)..(42)
<223> OTHER INFORMATION: Abeta 40(42)

<400> SEQUENCE: 16

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 17
<211> LENGTH: 37
<212> TYPE: PRT
<213> ORGANISM: Homo sapiens
```

```
<220> FEATURE:
<221> NAME/KEY: MISC_FEATURE
<222> LOCATION: (1)..(37)
<223> OTHER INFORMATION: IAPP
<220> FEATURE:
<221> NAME/KEY: SITE
<222> LOCATION: 2,7
<223> OTHER INFORMATION: disulfide bond between position 2 and 7

<400> SEQUENCE: 17

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 18
<211> LENGTH: 21
<212> TYPE: PRT
<213> ORGANISM: Artificial Sequence
<220> FEATURE:
<223> OTHER INFORMATION: R3-GI
<220> FEATURE:
<221> NAME/KEY: MOD_RES
<222> LOCATION: 17,19
<223> OTHER INFORMATION: N-Methylation

<400> SEQUENCE: 18

Ala Thr Gln Arg Leu Ala Asn Phe Leu Val His Arg Arg Asn Phe
1               5                   10                  15

Gly Ala Ile Leu Ser
            20

<210> SEQ ID NO 19
<211> LENGTH: 23
<212> TYPE: PRT
<213> ORGANISM: Artificial Sequence
<220> FEATURE:
<223> OTHER INFORMATION: synthesized
<220> FEATURE:
<221> NAME/KEY: SITE
<222> LOCATION: 1,23
<223> OTHER INFORMATION: disulfide bond between position 1 and 23
<220> FEATURE:
<221> NAME/KEY: MOD_RES
<222> LOCATION: 18,20
<223> OTHER INFORMATION: N-Methylation

<400> SEQUENCE: 19

Cys Ala Thr Gln Arg Leu Ala Asn Phe Leu Val His Arg Arg Arg Asn
1               5                   10                  15

Phe Gly Ala Ile Leu Ser Cys
            20

<210> SEQ ID NO 20
<211> LENGTH: 4
<212> TYPE: PRT
<213> ORGANISM: Artificial Sequence
<220> FEATURE:
<223> OTHER INFORMATION: synthesized
<220> FEATURE:
<221> NAME/KEY: MOD_RES
<222> LOCATION: 2,4
<223> OTHER INFORMATION: N-Methylation
<220> FEATURE:
<221> NAME/KEY: VARIANT
<222> LOCATION: 3
<223> OTHER INFORMATION: Unspecified amino acid
```

```
<400> SEQUENCE: 20

Phe Gly Xaa Ile
1

<210> SEQ ID NO 21
<211> LENGTH: 12
<212> TYPE: PRT
<213> ORGANISM: Artificial Sequence
<220> FEATURE:
<223> OTHER INFORMATION: synthesized
<220> FEATURE:
<221> NAME/KEY: MOD_RES
<222> LOCATION: 12
<223> OTHER INFORMATION: AMIDATION

<400> SEQUENCE: 21

Thr His Arg Pro Pro Met Trp Ser Pro Val Trp Pro
1               5                  10
```

AMYLOID INHIBITORY PEPTIDES

CROSS REFERENCE TO RELATED APPLICATIONS

This application is a National Stage Application of International Application Number PCT/EP2019/064793, filed Jun. 6, 2019; which claims priority to European Application No. 18176609.8, filed Jun. 7, 2018.

The Sequence Listing for this application is labeled "SeqList-14Jan21-ST25.TXT", which was created on Jan. 14, 2021 and is 10 KB. The entire content is incorporated herein by reference in its entirety.

The present invention relates to peptides, in particular amyloid inhibitory peptides, and to pharmaceutical compositions comprising such peptides. Furthermore, the present invention relates to such peptides, in particular such amyloid inhibitory peptides, for use in methods of treating or diagnosing neurodegenerative diseases such as Alzheimer's disease, or for use in a method of treating or diagnosing type 2 diabetes. Furthermore, the present invention also relates to a kit for the in-vitro or in-vivo detection and, optionally, quantification of amyloidogenic polypeptides, amyloid fibrils or amyloid aggregates, and/or for the diagnosis of Alzheimer's disease or type 2 diabetes in a patient.

Amyloid self-assembly is linked to devastating cell-degenerative diseases including Alzheimer's disease (AD) and type 2 diabetes (T2D). Molecules blocking amyloidogenesis of the key amyloid polypeptides of AD and T2D amyloid-β peptide (Aβ40(42)) (AD) and islet amyloid polypeptide (IAPP) (T2D) could thus become drug candidates. However, the rational design of amyloid inhibitors is a difficult task. Major reasons are the high conformational flexibility of most amyloidogenic polypeptides, high affinity interactions of amyloid self-assembly, and the large size of involved interfaces. Additional challenges include a low blood-brain-barrier (BBB) permeability, high production costs, and potential immunogenicity of antibodies, low proteolytic stability and usually no BBB crossing of linear peptides, while small molecules often lack high affinity and specificity and cannot block interactions involving large interfaces. Importantly, none of the reported inhibitors of amyloid self-assembly of Aβ40(42) or IAPP has yet advanced to the clinic.

Accordingly, there is a need for new inhibitors of amyloid self-assembly of Aβ40(42) or IAPP. There is furthermore a need to provide amyloid inhibitors that are specific for amyloid self-assembly of Aβ40(42).

In a first aspect, the present invention relates to a peptide, preferably an amyloid inhibitory peptide, having an amino acid sequence according to formula 0

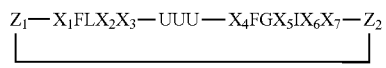

(Formula 0)

wherein

Z1 and Z2 are selected from the following pairs
 a) cysteine and cysteine,
 b) aspartic acid and lysine, or lysine and aspartic acid,
 c) aspartic acid and ornithine, or ornithine and aspartic acid,
 d) aspartic acid and 2,4-diaminobutyric acid, or 2,4-diaminobutyric acid and aspartic acid,
 e) aspartic acid and 2,3-diaminopropionic acid, or 2,3-diaminopropionic acid and aspartic acid, f) glutamic acid and lysine, or lysine and glutamic acid,
 g) glutamic acid and ornithine, or ornithine and glutamic acid,
 h) glutamic acid and 2,4-diaminobutyric acid, or 2,4-diaminobutyric acid and glutamic acid,
 i) glutamic acid and 2,3-diaminopropionic acid, or 2,3-diaminopropionic acid and glutamic acid;

with ⌐⌐ denoting a covalent bond between Z1 and Z2, thus providing for a cyclization of the peptide;

X1, X2, X3, X4, X5, X6, and X7 are, independently at each occurrence, selected from glycine, asparagine, valine, histidine, leucine, serine, alanine, and threonine;

F is, independently at each occurrence, phenylalanine;

L is leucine;

U is, independently at each occurrence, selected from arginine, homoarginine, citrulline, ornithine, lysine, and norleucine;

G is glycine;

I is isoleucine;

wherein Z1, Z2, X1-X7, F, L, U, G and I are L-amino acid residues or D-amino acid residues, or some of Z1, Z2, X1-X7, F, L, U, G and I are L-amino acid residues and others are D-amino acid residues;

and pharmaceutically acceptable salts, esters, solvates, polymorphs and modified forms thereof;

wherein preferably said peptide has an amino acid sequence according to formula 0a

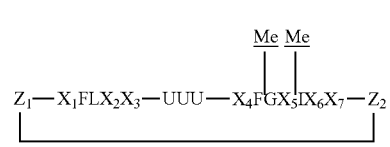

(Formula 0a)

wherein
Z1, Z2, X1-X7, F, L, U, G, I are as defined above, and

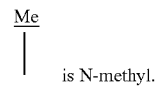

is N-methyl.

In one embodiment, the peptide according to the present invention, preferably the amyloid inhibitory peptide according to the present invention, has an amino acid sequence according to formula 1

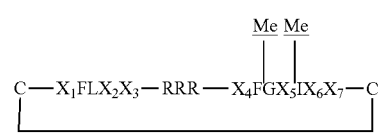

(Formula 1)

or an amino acid sequence according to formula 1*

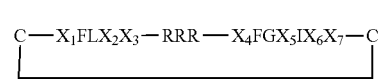

(Formula 1*)

wherein
C is cysteine;
X1, X2, X3, X4, X5, X6, and X7 are, independently at each occurrence, selected from glycine, asparagine, valine, histidine, leucine, serine, alanine, and threonine;
F is, independently at each occurrence, phenylalanine;
L is leucine;
R is arginine;
G is glycine;
I is isoleucine;
 is a disulfide bond;

is N-methyl;
C, X1-X7, F, L, R, G and I are L-amino acid residues or D-amino acid residues, or some of C, X1-X7, F, L, R, G and I are L-amino acid residues and others are D-amino acid residues;
and pharmaceutically acceptable salts, esters, solvates, polymorphs and other modified forms thereof.

In an embodiment of the peptide, either
a) X1 and X4 are asparagine, X2 is valine, X3 is histidine, X4 is glycine, X5 is glycine, X6 and X7 are glycine;
b) X1-X7 are glycine, alanine or serine;
c) X1-X7 are glycine;
d) X1-X3 are glycine, X4 is asparagine, X5 is alanine, and X6-X7 are glycine; or
e) X1-X3 are glycine, X4 is asparagine, X5 is alanine, X6 is leucine, X7 is serine.

In one embodiment, Z1, Z2, C, X1-X7, F, L, U, R, G, and I are L-amino acid residues.

In one embodiment, R is, at each occurrence, D-arginine, and/or

F is, at each occurrence, D-phenylalanine, and/or L is D-leucine, and/or

Z1, Z2 and C are D-amino acid residues, and/or

I is D-isoleucine or N-methyl-D-isoleucine.

In one embodiment, the peptide according to the present invention has a sequence according to a formula selected from the following formulae 2a-2e, 2a*-2e*:

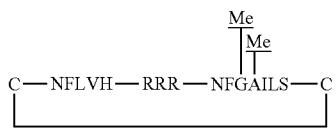 (Formula 2a)

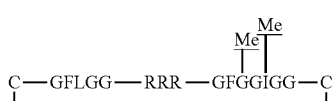 (Formula 2b)

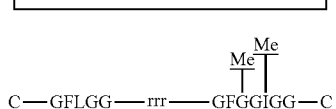 (Formula 2c)

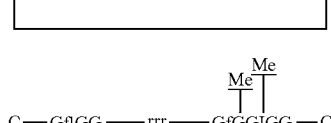 (Formula 2d)

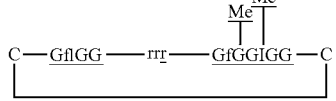 (Formula 2e)

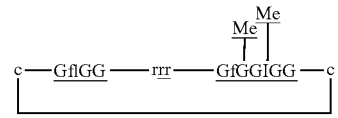 (Formula 2e)

C—NFLVH—RRR—NFGAILS—C (Formula 2a*)

C—GFLGG—RRR—GFGGIGG—C (Formula 2b*)

C—GFLGG—rrr—GFGGIGG—C (Formula 2c*)

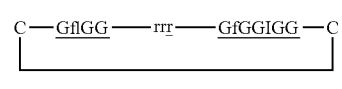 (Formula 2d*)

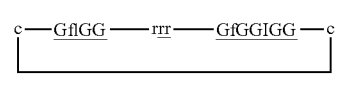 (Formula 2e*)

wherein upper case letters represent L-amino acid residues or D-amino acid residues, preferably L-amino acid residues, and lower case letters represent D-amino acid residues.

In a particularly preferred embodiment, the peptide according to the present invention has a sequence according to a formula selected from 2e and 2e*

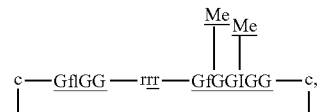 (Formula 2e)

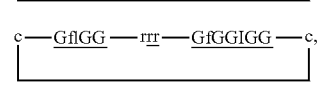 (Formula 2e*)

wherein upper case letters represent L-amino acid residues or D-amino acid residues, preferably L-amino acid residues, and lower case letters represent D-amino acid residues.

In one embodiment, said peptide consists of a sequence according to any of formulae 0, 0a, 1, 1*, 2a-2e, 2a*-2e*, as defined above, respectively.

In one embodiment, said peptide is an amyloid inhibitory peptide that preferably binds to Aβ40(42) and/or to islet amyloid polypeptide (IAPP), or said peptide is a peptide that binds to Aβ40(42) and/or to islet amyloid polypeptide (IAPP), but is not necessarily an amyloid inhibitory peptide.

It should be noted that in preferred embodiments, where reference is made to a "peptide" in general, such peptide may also be referred to as an "amyloid inhibitory peptide". An "amyloid inhibitory peptide" is a peptide that functions as or can be used as an "amyloid inhibitor".

Without wishing to be bound by any theory, the present inventors believe that the amyloid inhibitory effect of an amyloid inhibitory peptide is mediated by its binding to key amyloid polypeptides, in particular to Aβ40(42) and/or to islet amyloid polypeptide (IAPP).

Hence, the term "amyloid inhibitory" as used herein in the context of a peptide, refers to the capability of such peptide to block or inhibit amyloid self-assembly or amyloidogenesis, preferably of the key amyloid polypeptides, in particular of Aβ40(42) and/or of islet amyloid polypeptide (IAPP).

Amyloid inhibitory peptides in accordance with the present invention are useful as amyloid inhibitors, and may thus be used for therapeutic and/or diagnostic purposes, i.e. they may be used for treatment and/or diagnosis of diseases involving amyloid self-assembly or amyloidogenesis, in particular of Alzheimer's disease and/or of type 2 diabetes.

In other embodiments, a peptide in accordance with the present invention may have the capability to bind to key amyloid polypeptides, but may not necessarily be capable of functioning as an amyloid inhibitor. Such peptides may herein also sometimes be referred to as "amyloid binding peptides". They bind to key amyloid peptides, but are not capable of blocking or inhibiting amyloid self-assembly or amyloidogenesis. They may nevertheless be useful for detection purposes, in cases where detection of amyloid peptides may be desirable.

In a further aspect, the present invention also relates to a composition comprising a peptide, preferably an amyloid inhibitory peptide, according to the present invention, and a suitable solvent, such as water, and a buffer.

In a further aspect, the present invention also relates to a pharmaceutical composition comprising a peptide, preferably an amyloid inhibitory peptide, according to the present invention and a pharmaceutically acceptable excipient.

In such pharmaceutical composition, the peptide may occur as such, or it may be linked to other entities/molecules that endow the peptide with a specific functionality. For example, there may be a tag attached to increase blood-brain-barrier permeability, or it may be attached to a specific reporter molecule, such as a dye or a quantum dot, allowing the detection in diagnostic methods (preferably whilst retaining the therapeutic functionality of the peptide—"theranostic applications"). The use of quantum dots may be particularly useful in various imaging technologies, such as MRI, PET, PET-MRI, or specifically quantum-dot-based brain imaging methodologies. In certain embodiments, the peptide may be attached to a nanoparticle, to a suitable carrier molecule, to a targeting entity or other functional molecule.

Because the peptides according to the present invention are capable of passing the blood-brain-barrier, the present invention also relates to the use of a peptide according to the present invention, as defined above, as a carrier for molecules, substances or compounds to pass the blood-brain-barrier. According to this aspect, in certain embodiments, the molecule to pass the blood-brain-barrier is linked, preferably covalently linked, to a peptide according to the present invention as defined above.

In a further aspect, the present invention also relates to a peptide, in particular an amyloid inhibitory peptide, according to the present invention, or the pharmaceutical composition according to the present invention as defined above, for use in a method of treating Alzheimer's disease or for use in a method of treating type 2 diabetes.

In one embodiment of such peptide or composition for use, said method comprises administering an effective amount of said peptide or of said composition to a patient in need thereof.

In a further aspect, the present invention also relates to a peptide, in particular an amyloid inhibitory peptide, according to the present invention, or the pharmaceutical composition according to the present invention as defined above, for use in a method of diagnosing Alzheimer's disease or for use in a method of diagnosing type 2 diabetes.

In one embodiment of such peptide or composition for use, said method comprises administering an effective amount of said peptide or of said composition to a subject to be tested for Alzheimer's disease or type 2 diabetes.

In one embodiment of such peptide or composition for use, said peptide, in particular said amyloid inhibitory peptide, is linked to or administered together with a suitable reporter molecule that allows detection of Aβ40(42), islet amyloid polypeptide (IAPP) and/or amyloid aggregates thereof, by a suitable detection methodology, such as positron emission tomography (PET), nuclear magnetic resonance (NMR), magnetic resonance imaging (MRI), and PET-MRI and said subject, after administration of said peptide, is subjected to PET, NMR, MRI, PET-MRI.

In a yet a further aspect, the present invention relates to a kit for the in-vitro or in-vivo detection of amyloid fibrils or aggregates and/or for the quantification thereof, or for the diagnosis of Alzheimer's disease or type 2 diabetes in a patient, said kit comprising the peptide, in particular the amyloid inhibitory peptide according to the present invention as defined above, in a freeze-dried form in a suitable container, a buffered solvent in a separate container for reconstitution of said peptide in solution, and, optionally, means to dispense said peptide once reconstituted in solution, such as a syringe or pipette. Alternatively, the kit may contain the peptide, in particular the amyloid inhibitory peptide according to the present invention as defined above, in an already reconstituted, ready-to-use form.

In a yet a further aspect, the present invention also relates to the use of the peptide according to the present invention, in an in-vitro assay, such as an enzyme linked immunosorbent assay (ELISA) or a radioimmuno assay (RIA), for the detection of monomeric islet amyloid polypeptide (IAPP), monomeric Aβ40(42), amyloid fibrils, or amyloid aggregates. Such use may, in certain embodiments, involve the analysis of blood, cerebrospinal fluid, or brain biopsies, and may also further involve the use of suitable reporter molecules to which the peptide may be attached or with which the peptide may be used together.

In a further aspect, the present invention relates to the use of a peptide according to the present invention, as defined above, for the manufacture of a medicament for the treatment or diagnosis of Alzheimer's disease or of type 2 diabetes.

In yet a further aspect, the present invention also relates to a method of treatment or diagnosis of Alzheimer's disease or type 2 diabetes, wherein said method comprises administering an effective amount of said peptide or of said composition according to the present invention as defined further above, to a patient in need thereof or to a subject to be tested.

The present inventors have provided cyclic peptides which function as nanomolar inhibitors of amyloid self-assembly of both Aβ40(42) or IAPP, or of Aβ40(42) alone, and which therefore have manifold applications.

Moreover, several of these peptides bind, with high affinity Aβ40(42) and/or IAPP monomers and/or amyloid aggregates.

In the present application, use is made of the one-letter-code for amino acid residues and the three-letter-code for amino acid residues. Hence, amino acid residues are designated herein by reference to their respective one-letter-code or three-letter-code. Accordingly, alanine is A or Ala; arginine is R or Arg; asparagine is N or Asn; aspartic acid is D or Asp; cysteine is C or Cys; glutamine is Q or Gln; glutamate is E or Glu; glycine is G or Gly; histidine is H or His; isoleucine is I or Ile; leucine is L or Leu; lysine is K or Lys; methionine is M or Met; phenylalanine is F or Phe;

proline is P or Pro; serine is S or Ser; threonine is T or Thr; tryptophan is W or Trp; tyrosine is Y or Tyr; valine is V or Val.

Sometimes, in this application, reference to amino acid sequences is made by reciting the individual residues. Where such amino acid sequence is indicated by using upper case letters only, this means that these amino acids are unspecified in terms of their chirality, i.e. the residues may be L-amino acids or D-amino acids or a mixture of the two possibilities, i.e. some of the residues in the sequence may be L-amino acids and others may be D-amino acids. In one embodiment, the upper case amino acids may be all L-amino acids.

In those instances, where such amino acid sequence is indicated by using upper case letters and lower case letters together in one sequence, this means that the upper case amino acids may be L-amino acids or D-amino acids, preferably L-amino acids, and the lower case amino acids are, in any case, D-amino acids.

Moreover, sometimes, in this application, reference to amino acid sequences is made by reciting the individual residues as free amino acids, such as "glycine", "glutamic acid", etc., notwithstanding the fact that these residues appear in the respective amino acid sequence in their respective covalently linked form, i.e. with the individual residues linked by appropriate peptide bonds, i.e. amide bonds, between them.

The term "N-methyl" or "NMe" or

as used herein, refers to a methyl group that is attached to the nitrogen in the amide bond between two amino acid residues.

For example where a sequence is indicated as

this means that a methyl group is attached to the amide nitrogen forming the amide bond between F and G, and a further methyl group is attached to the amide nitrogen forming the amide bond between X and I. This may also be referred to as "N-methylated glycine" and "N-methylated isoleucine" respectively, or "methylated glycine" and a "methylated isoleucine", respectively, because the respective amide nitrogen belongs to glycine and isoleucine respectively in these cases.

In some preferred embodiments of the peptide according to the present invention, there is a methyl group attached to the amide bond between F11 and G12 (i.e. a "methylated glycine 12"), and a further methyl group attached to the amide bond between X13 and I14 (i.e. a "methylated isoleucine 14"), if one uses a numbering which is based on a 17-peptide according to any of formulae 0, 0a, 1, 1*, 2, 2a-2e, 2a*-2e*. By reference to the IAPP-numbering, these positions correspond to the amide bond between F23 and G24 and the amide bond between A25 and I26.

The symbol ⌊⌋ refers to a covalent bond between two residues thus linked. For example, if the two residues thus linked are two cysteines, it means a disulfide bond.

Alternatively, it may mean a lactam bridge involving the sidechains of the respective two amino acids. For example, the sidechains of aspartic acid and lysine, or of glutamic acid and lysine may form such a lactam bridge. Pairs that may be involved in such lactam bridge formation are Asp-Lys, Asp-Orn, Asp-Dab (Dab meaning 2,4 diaminobutyric acid), Asp-Dap (Dap meaning 2,3-diaminopropionic acid), Glu-Lys, Glu-Orn, Glu-Dab, Glu-Dap, or pairs with an inverse arrangement of the aforementioned residues. In one embodiment, it also possible to obtain a cyclisation via the generation of 1,2,3-triazole rings, generated by click reactions between specific amino acids, instead of cysteines.

In one embodiment, the N-terminus and/or the C-terminus of the peptides according to the present invention are protected. Suitable protecting groups are manifold and are known to a person skilled in the art. For example, the N-terminus may be acetylated or formylated, or there may be an even longer chain attached such as palmitoyl. The C-terminus could be protected via formation of an amide or carbonic acid ester. In one embodiment, the C-termini of the peptide(s) according to the present invention, in particular of the amyloid inhibitory peptides according to the present invention, more particularly of the peptides according to formulae 0, 0a, 1, 1*, 2a-2e, 2a*-2e* according to the present invention, are protected by an amide. In other embodiments, the C-terminus is in its free carboxy-form; in yet other embodiments, it is in esterified form. In particularly preferred embodiments, the C-termini of the peptide(s) according to the present invention, in particular of the amyloid inhibitory peptides according to the present invention, more particularly of the peptides according to formulae 0, 0a, 1, 1*, 2a-2e, 2a*-2e* according to the present invention, are protected by an amide, and the respective N-termini of the peptides are unprotected, i.e. in their $NH_2$-form (or $NH_3^+$-form).

The term "treatment" or "treating", as used herein, encompasses both prophylactic treatment and therapeutic treatment. In a preferred embodiment, it specifically refers to therapeutic treatment.

The present inventors have managed to design peptidic inhibitors of amyloid self-assembly of both Aβ40(42) and IAPP, or of Aβ40(42) alone. Without wishing to be bound by any theory, the present inventors believe that the peptidic inhibitors according to the present invention mimic IAPP interaction surfaces while maintaining only minimal IAPP-derived self/cross-recognition elements. Most interestingly, a switching of chiralities of certain residues led to an inhibitor that was specifically selective for Aβ40(42) and which, in addition, exhibited both strongly improved proteolytic stability in human plasma and blood-brain-barrier crossing ability in a cell model.

Furthermore, reference is made to the figures, wherein

FIG. 1 shows an embodiment of the inhibitor design strategy employed by the present inventors. a) shows the sequences of Aβ40(42) and IAPP. b) shows a partial sequence from IAPP, R3-GI (1) (a peptide based on residues 8-28 of IAPP) and designed peptides with lower-case-letters denoting D-amino acid residues. There are amide bond N-methylations at G12 and I14.

Figure 2:
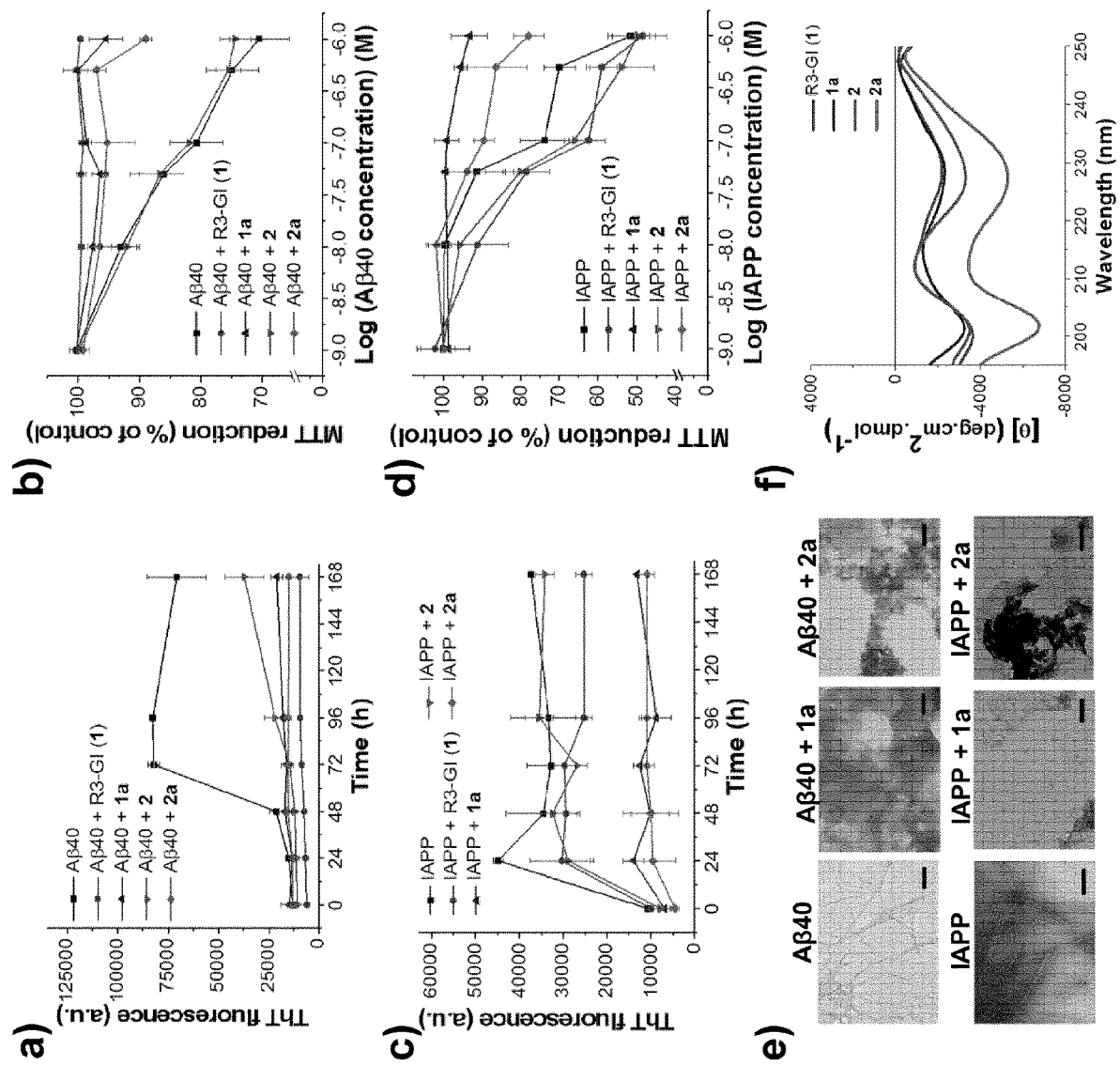

FIG. 2 shows the effects of effects of peptides 1-2a on amyloid self-assembly of Aβ40 and IAPP and CD studies on their conformations. a) Fibrillogenesis of Aβ40 (16.5 μM) or its mixtures (Aβ40/peptide, 1/1 or 1/2 (2)) by ThT binding (means (±SD), 3 assays). b) Effects on cell viability: Solutions from 1a (7 day-aged) added to PC12 cells; cell damage determined by MIT reduction (means (±S.D.), 3 assays (n=3 each)). c) Fibrillogenesis of IAPP (6 μM) and its mixtures (IAPP/peptide, 1/2 (1a, 2a) or 1/10 (1, 2) by ThT binding (means (±S.D.), 3 assays). d) Cell-damaging effects of IAPP or its mixtures (from 1c; 7 day-aged) on RIN5fm cells via MIT reduction (means (±S.D.), 3 assays (n=3 each)). e) TEM images of Aβ40, IAPP and their mixtures with is and 2a (7 days aged) (bars wo nm). f) CD spectra (5 μM, pH 7.4).

Figure 3:
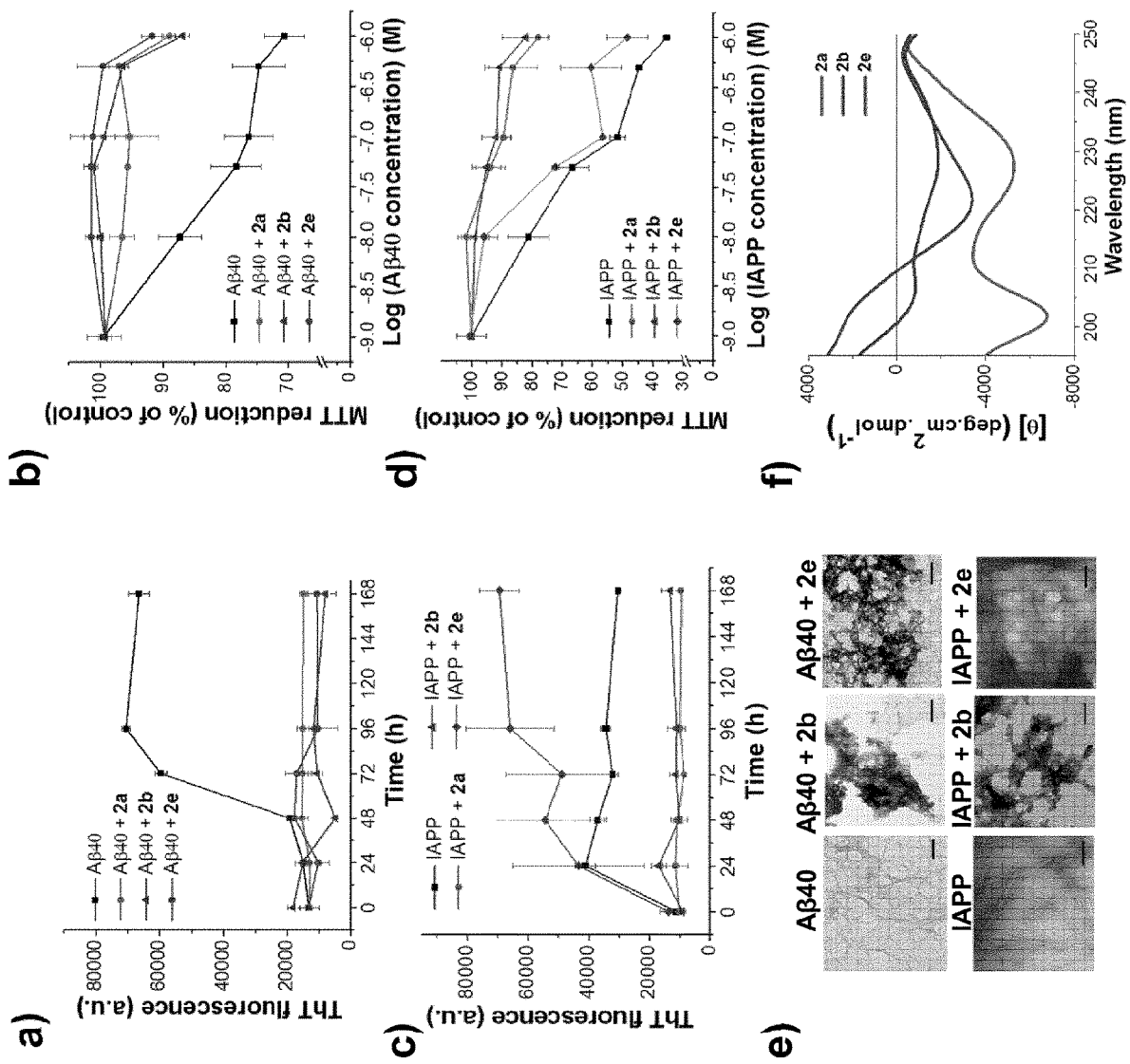

FIG. 3 shows effects of peptides 2b and 2e versus 2a on fibrillogenesis and cytotoxicity of Aβ40 and IAPP and CD studies on inhibitor conformations. a) Fibrillogenesis of Aβ40(16.5 μM) or its mixtures with 2a (1/1) and 2b or 2e (1/5) by ThT binding (means (±S.D.), 3 assays). b) PC12 cell viability following treatment with 7 day-aged solutions (from 2a) by MIT reduction (means (±S.D.), 3 assays (n=3 each)). c) Fibrillogenesis of IAPP (6 μM) or its mixtures with 2a (1/2) and 2b or 2e (1/10) determined by ThT binding (means (±S.D.), 3 assays). d) RIN5fm cell viability following treatment with 7 day-aged solutions (from 2c) by MIT reduction (means (±SD), 3 assays (n=3 each)). e) TEM images of Aβ40 or IAPP and their mixtures with 2b and 2e (7 day-aged) (bars 100 nm). f) CD spectra (5 μM, pH 7.4).

Figure 4:
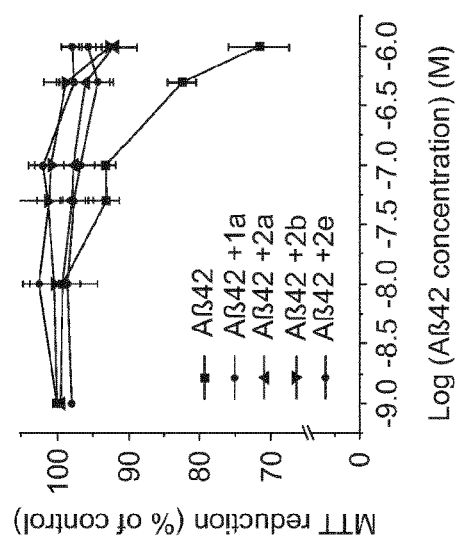
Figure 4:
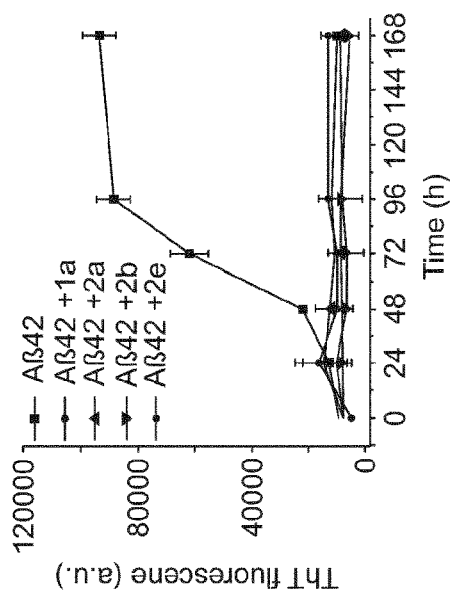
Figure 4:
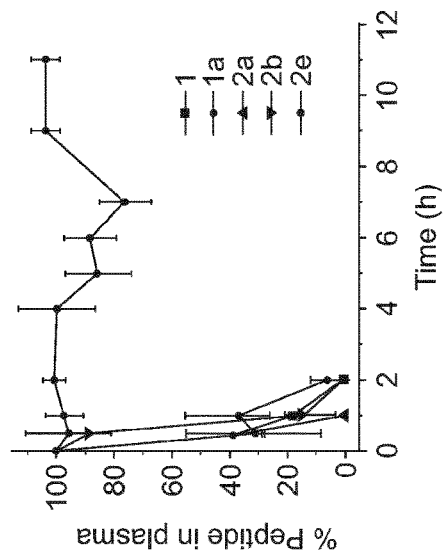
Figure 4:
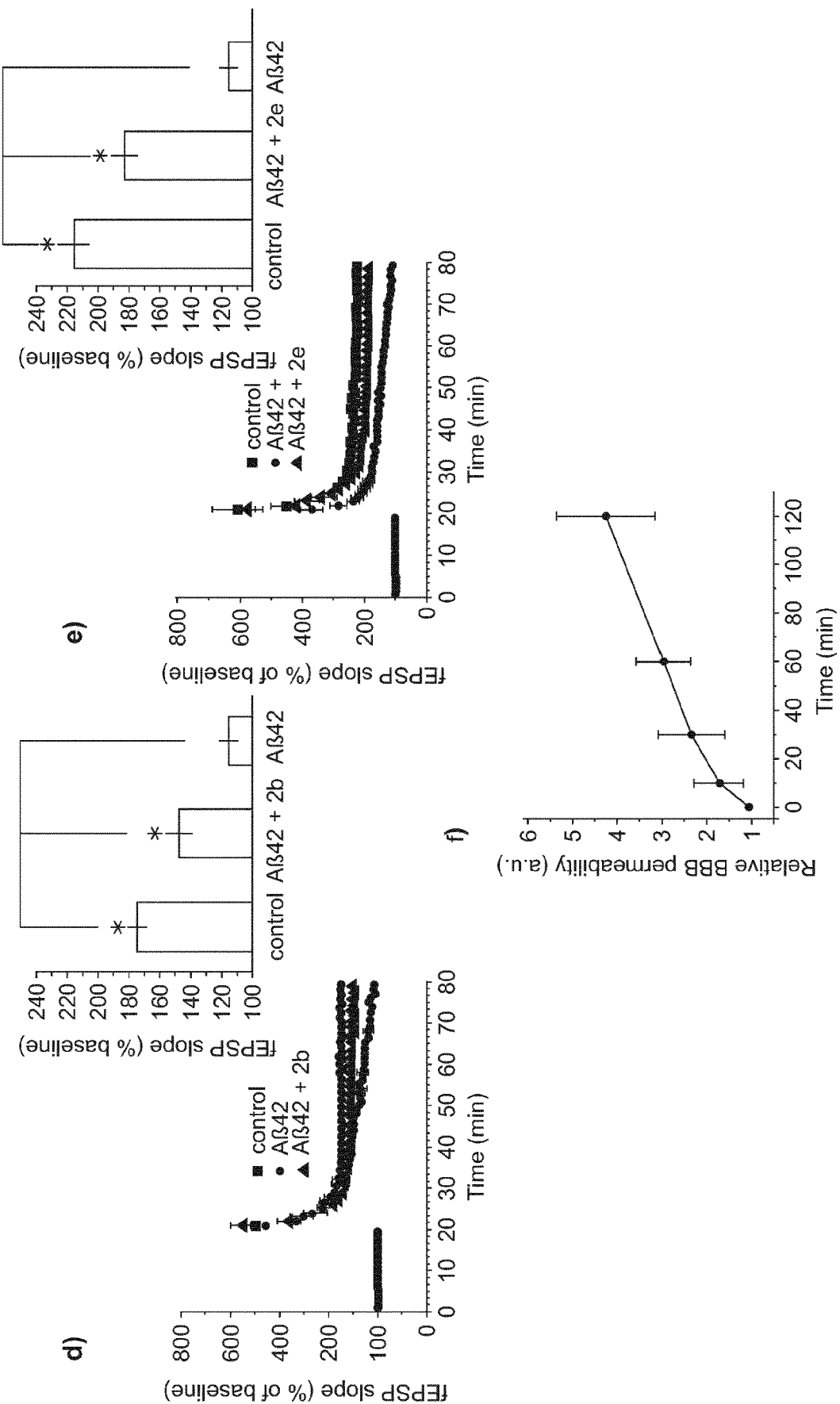
Figure 4:
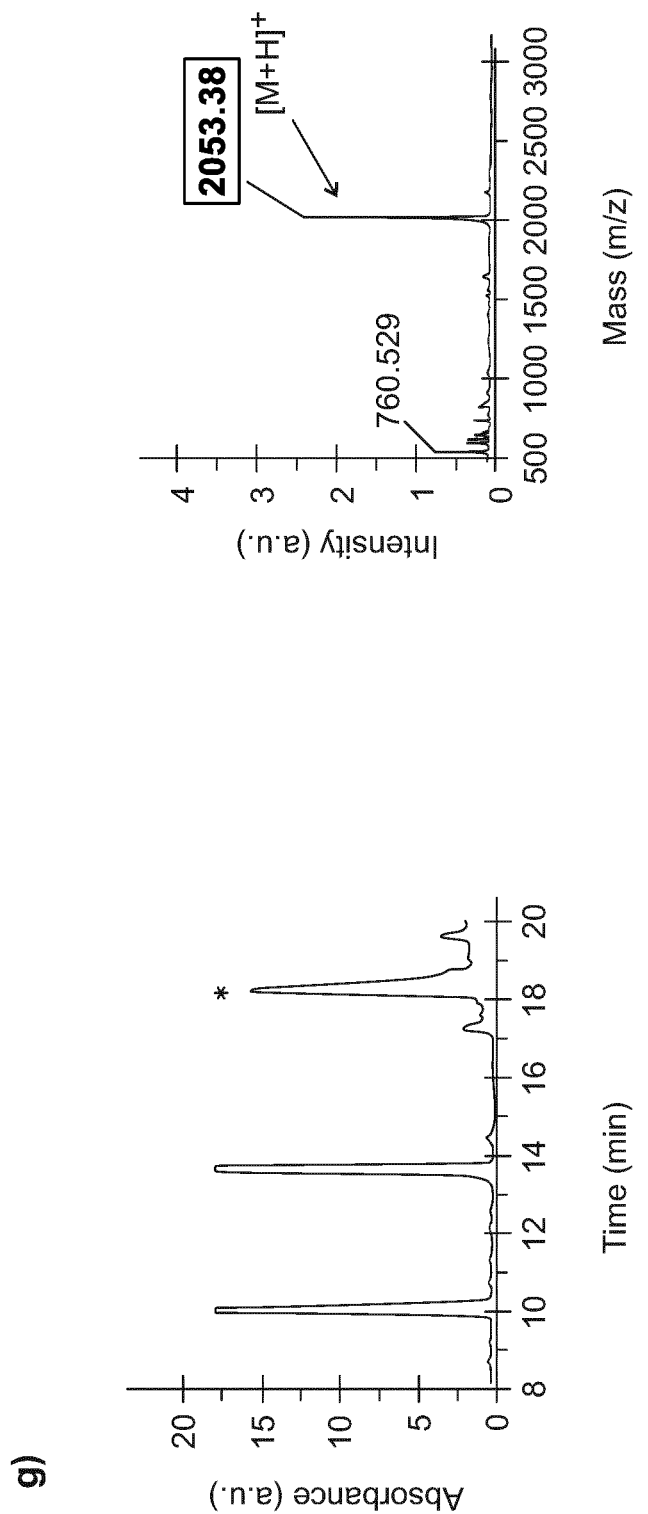

FIG. 4 shows proteolytic stabilities of inhibitors in human blood plasma in vitro (a), effects on Aβ42 amyloid self-assembly (b,c) and on Aβ42-induced impairment of synaptic LTP ex vivo (d,e), and permeability across a human BBB model in vitro (f,g). a) Peptides were incubated in plasma and quantified by HPLC and MALDI-TOF-MS; remaining intact peptide (% of total) is plotted over incubation time. b) Fibrillogenesis of Aβ42 (16.5 μM) or its mixtures with peptides (1a & 2a, 1/1; 2b & 2e, 1/5) by ThT binding (means (±SD), 3 assays). c) PC12 cell viability after treatment with 7 day-aged solutions from 3b by MIT reduction (means (±SD), 3 assays (n=3)). d,e) Amelioration of Aβ42-induced (50 nM) LTP impairment in murine acute hippocampal slices by 2b (d) or 2e (e) (500 nM). Time course of synaptic transmission (means (±SEM), n=7 (Aβ42/inhibitor mixtures), n=4 (Aβ42) and n=9-11 (control). Inset: LTP in presence of Aβ42, Aβ42/inhibitor mixture, or inhibitor alone (control) as above; bars show average from the last 5 min of recordings (means (±SEM), n=7-14); * indicates significant effects for the mixtures or controls versus Aβ42 ($p<0.05$, n=7-11 (unpaired t-test). f) Relative permeability of 2e (Fluos-2e; 10 μM) across the BBB cell model; plot shows Fluos-2e amount in acceptor chamber at various time points (means (±SEM), n=3-4). g) RP-HPLC chromatogram of solution in acceptor chamber at 2 h (from 3f) (left) and MALDI-TOF spectrum (right) of peptide eluted at ~18 min (*, Fluos-2e, calculated $[M+H]^+$=2053.20, found 2053.38); additional peaks are from assay medium.

Moreover, reference is made to the following examples which are given to illustrate and not to limit the present invention.

EXAMPLES

Example 1—Materials and Methods

Peptides and Peptide Synthesis

Aβ40 (TFA salt) was synthesized by Fmoc-based solid phase synthesis (SPPS) on Tentagel R PHB resin (Rapp Polymere) using previously published protocols, purified by RP-HPLC and treated as described. Aβ40 stocks were freshly prepared in 1,1,3,3,3,3-hexafluoro-2-isopropanol (HFIP) (4° C.); their concentrations were determined by the bicinchoninic acid (BCA) assay (Pierce). IAPP was synthesized by SPPS and the Fmoc-strategy on RINK resin, subjected to air oxidation and purified by RP-HPLC. Freshly made IAPP stocks in HFIP (200-500 μM) were filtered over 0.2 μm filters (Millipore) (4° C.); concentrations were determined by UV spectroscopy. $N^α$-terminal fluorescein-labeled IAPP (Fluos-IAPP) and N-terminal 7-diethylaminocoumarin-3-carbonyl-labeled Aβ40 (Dac-Aβ40) for fluorescence spectroscopic titrations were synthesized by Fmoc-based SPPS, purified and handled. Synthetic Aβ42 (TFA salt) was from PSL (Heidelberg) and its HFIP stocks were made. Synthetic N-terminal FITC-β-Ala-labeled Aβ42 (FITC-Aβ42) (FITC, fluorescein isothiocyanate) for fluorescence titrations was from Bachem; its HFIP stock solutions were always freshly made (4° C.) and their concentrations determined by UV spectroscopy. ISMs, MCIPs, control peptides (analogs of 2a and 2b), THRPPMWSPVWP-amide (Trfb) and their N-terminal fluorescein-labeled analogs (C-terminal amides) were synthesized by Fmoc-based SPPS on Rink-resin and cleaved from the resin using previously published protocols. Disulphide bridge formation of MCIPs and control peptides was performed by dissolving crude peptide (after cleavage and lyophilization) at 1 mg/ml in aqueous 0.1 M $NH_4HCO_3$ solution containing 40% DMSO; the progress of the oxidation reaction was followed by RP-HPLC. Peptides were purified by RP-HPLC using previously described protocols and characterized by MALDI-TOF mass spectrometry (MS) Stock solutions of all peptides were freshly made in HFIP (4° C.) and concentrations were determined by peptide weight and by UV spectroscopy in the case of fluorescently labeled peptides.

Thioflavin T (ThT) Binding Assays

To study the effects of peptides on Aβ40(42) and IAPP fibrillogenesis previously established ThT binding assay systems were used. Briefly, Aβ40 (16.5 μM) or IAPP (6 μM) and their mixtures with peptides were incubated for up to 7 days in ThT assay buffer at room temperature. The ThT assay buffer consisted of aqueous 50 mM sodium phosphate buffer, pH 7.4, containing 100 mM NaCl and 1% HFIP (Aβ40(42) related studies) or 0.5% HFIP (IAPP related studies). Each experimental set contained incubations of Aβ40(42) or IAPP alone as controls. At indicated time points, aliquots were gently mixed with a ThT solution (20 μM ThT in 0.05 M glycine/NaOH, pH 8.5); ThT binding was determined immediately by measuring fluorescence emission at 486 nm upon excitation at 450 nm using a 2030 Multilabel Reader VictorX3 (PerkinElmer Life Sciences). Effects of peptides added at specific pre- and post-nucleation time points of Aβ40 amyloidogenesis were studied by adding aliquots of Aβ40 solutions (16.5 μM; incubation conditions as above) aged for the indicated time points to the peptide (in dry form) as previously described and ThT binding was determined as above. To determine the effects of peptides on already nucleated IAPP fibrillogenesis, aliquots of IAPP (16.5 μM; incubation conditions as above), which was aged for the indicated time points and contained significant amounts of IAPP fibrils (as confirmed by ThT binding and TEM (data not shown)) was added to the peptide (in dry form) as described and ThT binding was determined as above.

Transmission Electron Microscopy (TEM)

10 μl aliquots of solutions of the ThT binding and MTT assays were applied on carbon-coated grids at indicated time points, washed with distilled water and stained with aqueous 2% (w/v) uranyl acetate as described. Grids were examined using a JEOL JEM 100CX (at 100 kV) or a JEOL 1400 Nus electron microscope (at 120 kV).

Assessment of Cell Damage by MTT Reduction Assay

Effects of peptides on the formation of cell-damaging IAPP or Aβ40(42) assemblies were studied using the solutions applied for the ThT binding assays as previously described. Briefly, for effects on the formation of cell-damaging Aβ40(42) aggregates, the inventors used cultured PC-12 cells while for effects on IAPP-mediated cell damage cultured RIN5fm cells were used. Both cell lines were cultured and plated in 96-well plates as described. Solutions consisting of Aβ40(42) or IAPP alone (16.5 and 6 µM, respectively) versus their mixtures with the potential inhibitors were made as described under "ThT binding assays" and incubated for 7 or 8 days at room temperature. At the incubation time points of 24 h or 72 h and 7 (or 8) days (identical results were obtained from solutions aged for 7 or 8 days), aliquots were diluted with cell culture medium and added to the cells at the indicated final concentrations. Following incubation with the cells for ~20 h (37° C., humidified atmosphere with 5% $CO_2$), the MTT reduction assay was used to assess cell damage/metabolic activity as previously described. To determine $IC_{50}$ values, Aβ40 (500 nM) or IAPP (100 nM) were titrated with different amounts of peptides under the conditions of the ThT binding assays and cell-damaging effects were determined using 24 h-aged solutions (IAPP-related effects) or 72 h-aged solutions (Aβ40-related effects) by the MIT assay as described. Of note, studies with selected MCIPs (incubated under the same conditions as in their mixtures with Aβ40(42) or IAPP) showed that they were, as expected, non-amyloidogenic and not cytotoxic (data not shown). These results were in line with the fact that the sequences of the MCIPs were derived from the non-amyloidogenic and non-cytotoxic ISM R3-GI and with results of previous studies showing the lack of amyloidogenicity and cell-damaging effects of related N-methylated IAPP analogs or segments.

To determine the effects of peptides on preformed cell damaging assemblies of Aβ40 or IAPP, aliquots of Aβ40 or IAPP solutions (16.5 µM; incubation conditions as above), aged for the indicated time points and containing significant amounts of cell damaging assemblies (as shown by the MIT reduction assay in this and previous studies (data not shown)) were added to the peptide (in dry form) as described and following incubation for the indicated time points solutions were added to PC12 or RIN5fm cells. Following incubation with the cells for ~20 h, the MIT reduction assay was performed as described. Of note, our assay system allows following in parallel formation of both fibrils (by the ThT binding assay) and cell damaging assemblies of Aβ40 (42) and IAPP starting from non-fibrillar and non-toxic states as previously described.

Far-UV CD Spectroscopy

Far-UV CD measurements were performed with a Jasco 715 spectropolarimeter as described. Spectra were measured immediately following solution preparation between 195 and 250 nm, at 0.1 nm intervals, a response time of 1 sec, each spectrum being the average of 3 spectra and at room temperature. CD measurements were performed using freshly made 5 µM solutions of ISMs in aqueous 10 mM sodium phosphate buffer, pH 7.4, containing 1% HFIP (CD assay buffer); peptides were diluted from freshly made stock solutions in HFIP into the aqueous assay buffer. Of note, the magnitudes of the CD spectra of all peptides/inhibitors depend on their concentrations due to the inherently strong self-association potential of peptides derived from the human IAPP sequence (data not shown). The spectrum of the buffer was subtracted from the CD spectra of the peptide solutions prior conversion of the raw data to mean residue ellipticities.

Fluorescence Spectroscopic Titration Studies

A JASCO FP-6500 fluorescence spectrophotometer was used for the fluorescence spectroscopic titrations, which were performed by using previously described experimental protocols. Briefly, for titrations of Fluos-IAPP and FITC-labeled Aβ42, excitation was at 492 nm and fluorescence emission spectra were recorded between 500 and 600 nm, while for titrations of Dac-Aβ40, excitation was at 430 nm and emission spectra were collected between 440 and 550 nm. App. $K_d$s of interactions of IAPP, Aβ40 and Aβ42 with the peptides were determined by titrating freshly made solutions of Fluos-IAPP (5 nM), Dac-Aβ40(10 nM) and FITC-Aβ42 (5 nM) with peptides as described. Of note, this assay system has been previously used for the determination of the affinities (app. $K_d$) of interactions of a number of inhibitors of IAPP and Aβ40(42) amyloid self-assembly with these highly amyloidogenic polypeptides and the affinity of the Aβ40(42)-IAPP interactions as well. Briefly, freshly made stock solutions of peptides and fluorescently labeled analogs in HFIP were used. Measurements were performed in 10 mM sodium phosphate buffer, pH 7.4 (i % HFIP) at room temperature within 2-5 min following solution preparation. Under these experimental conditions, freshly made solutions of Fluos-IAPP, Dac-Aβ40 and FITC-Aβ42 at the herein-applied low nanomolar concentrations contain mostly monomers. App. $K_d$s were estimated using 1/1 binding models as previously described. Of note, due to the inherently high self-assembly potentials of IAPP-derived peptides more complex binding models may also apply. Determined app. KdDs are means (+SD) from three binding curves.

Cross-Linking, NuPAGE and Western Blot Analysis

Cross-linking studies were performed using a previously established assay system used for the characterization of hetero-assemblies of Aβ40 and IAPP with IAPP and IAPP-derived inhibitors including ISMs as described.[1, 4] Briefly, Aβ40 or IAPP were incubated alone (30 µM) or in the presence of peptides (IAPP/peptide and Aβ40/peptide 1/10) in aqueous 10 mM sodium phosphate buffer, pH 7.4, at room temperature for 3 h (Aβ40 related studies) or 30 min (IAPP related studies). Thereafter, samples were cross-linked with aqueous glutaraldehyde (25%) (Sigma-Aldrich) and cross-linked hetero-complexes were precipitated with aqueous trichloroacetic acid (TCA) (10%); pellets were dissolved in NuPAGE sample buffer (w/o reducing agent), boiled (5 min) and NuPAGE electrophoresis in 4-12% Bis-Tris gels with MES running buffer was performed according to the manufacturer's (Invitrogen) recommendations. Equal amounts of Aβ40 or IAPP were loaded in all lanes. For peptide blotting onto nitrocellulose, a XCell II Blot Module blotting system (Invitrogen) was used. Aβ40 and Aβ40-containing complexes were revealed by Western blotting and a polyclonal rabbit anti-Aβ40 antibody (Sigma-Aldrich) while IAPP and IAPP-containing complexes by a polyclonal rabbit anti-IAPP antibody (Bachem) in combination with peroxidase (POD)-coupled secondary antibody (Amersham) and the Super Signal Duration ECL staining solution (Pierce).

Peptide Stability in Human Plasma (In Vitro)

Peptides were dissolved in human blood plasma (obtained from voluntary healthy donors) at a concentration of 200 µM and incubated at 37° C. for various time intervals. Following quenching (1/1) with aqueous trichloroacetic acid (10%), solutions were incubated on ice for 10 min, subjected to centrifugation to precipitate plasma proteins (20200 g; 4 min), and the supernatants were mixed (1/2) with a solution consisting of 80% HPLC buffer B and 20% HPLC buffer A (see below). To quantify intact peptide at different time points, solutions containing the supernatants were analyzed by RP-HPLC (detection at 214 nm) by using a Nucleosil 100 C18 column (Grace) (length 33 mm length, ID 8 mm, 7 µm particle size) with a flow rate of 2.0 ml/min and eluting buffers A, 0.058% (v/v) TFA in water, and B, 0.05% (v/v) TFA in 90% (v/v) $CH_3CN$ in water. The elution gradient was 10-90% B in A over 8 min; this step was followed by a 90-10% B in A over 3 min step to establish starting conditions. HPLC fractions were collected, lyophilized, and analyzed by MALDI-TOF-MS using a Bruker Daltonik MALDI-TOF MS instrument.

Peptide Stability Toward Degradation by Human Neprilysin (In Vitro)

Stabilities of 2e and 2b toward degradation by neprilysin was studied based on a previously published protocol: Briefly, peptides were incubated (100 µM) with recombinant human neprilysin (NEP) (500 ng/ml) (Sigma-Aldrich) in 10 mM Tris buffer, pH 6.5 and at 37° C. At indicated time points aliquots were quenched (1/1) with aqueous trichloroacetic acid (10%) and solutions were subjected to HPLC analysis and HPLC fractions were collected and analyzed by MALDI-TOF-MS as described under "Peptide stability in human plasma" (above).

Determination of Surface Neprilysin/CD10 Levels by Flow Cytometry

Both the human cerebral microvascular endothelial cell line hCMEC/D3 and human umbilical vein endothelial cells (HUVEC) were cultured on collagen type I-coated plates (BD Biosciences) in EndoGRO™-MV Complete Media Kit (Merck) supplemented with 1 ng/mL fibroblast growth factor-basic (bFGF) (Merck) and maintained at 37° C. in a humidified atmosphere of 5% $CO_2$. Cell culture medium was routinely replaced every 2-3 days.

The cell surface expression of human CD10, also termed CALLA or neprilysin, on hCMECs and HUVECs was monitored by flow cytometry. Briefly, $1 \times 10^6$ cells were washed three times with ice-cold phosphate-buffered saline (PBS) supplemented with 0.5% bovine serum albumin (BSA) and subsequently stained with phycoerytherin (PE)-conjugated anti-CD10 antibody (eBioscience) or the corresponding isotype control IgG for 1 h at 4° C. After incubation, the cells were washed and analyzed by a BD FACSVerse™ flow cytometer (BD Biosciences). The quantification of the measurements was performed using FlowJo software.

Hippocampal Long-Term Potentiation (LTP) Measurements (Ex Vivo)

LTP measurements were performed as follows: Briefly, sagittal hippocampal slices (thickness: 350 µm) were obtained from adult (2 months) C57/BL6 male mice. Protocols were approved by the ethical committee on animal care and use of the government of Bavaria, Germany. Mice were anaesthetized by inhalation of isoflurane before decapitation and brains were rapidly removed. Hippocampal slices were prepared in ice-cold Ringer solution, placed in a holding chamber for at least 90 min—the first 30 min at 35° C., the following 60 min cooled down to room temperature—and then transferred to an immersion superfusing chamber for extracellular recordings. The flow rate of the solution through the chamber was 5-8 ml/min. The composition of the Ringer solution was 124 mM NaCl, 3 mM KCl, 26 mM $NaHCO_3$, 2 mM $CaCl_2$, 1 mM $MgSO_4$, 25 mM D-glucose, and 1.24 mM $NaH_2PO_4$; solution was bubbled with a mixture of 95% $O_2$ and 5% $CO_2$, and its pH was 7.3±0.1. Extracellular recordings were made by glass microelectrodes (2-3 MO filled with artificial cerebrospinal fluid (ACSF) and all measurements were performed at room temperature. Synthetic Aβ42 was freshly dissolved in ACSF and added to the bath solution (50 nM).

Field excitatory postsynaptic potentials (fEPSPs) were evoked by stimulating the Schaffer collateral commissural pathway (Sccp) in the dendritic region of hippocampal CA1 as described. For LTP induction, high-frequency stimulation (HFS; 100 Hz/100 pulses) conditioning pulses were delivered to the same Sccp inputs. For most recordings, both stimulating electrodes were used to utilize the input specificity of LTP and allowing the measurement of an internal control within the same slice. Aβ42 alone (50 nM) was applied for 90 min before high-frequency stimulation (HFS), providing time for its oligomerisation. Mixtures of Aβ42 (50 nM) with each of the tested peptides 2a, 2b and 2e (500 nM) were also applied for 90 min before HFS. Peptides alone (500 nM) were applied to the slices 1 h before HFS. Responses were measured for 60 min after HFS. Recordings were processed and data re-analysed as described. fEPSP slopes measurements were taken between 20 and 80% of the peak amplitude and EPSP slopes are presented as % EPSP slope of baseline (20 min control period before tetanic stimulation (100%)). Data were analysed by paired t-test.

Human BBB Transwell Permeability Assay (In Vitro)

Human cerebral microvascular endothelial (hCMEC/D3) cells (Merck) were cultured in collagen type I-coated dishes in EndoGro-MV complete culture media kit supplemented with 1 ng/mL fibroblast growth factor-2 (FGF-2) (all reagents from Merck) (at 37° C. and 5% $CO_2$). Of note, confluent hCMEC monolayers in Transwell filters represent a suitable model of the human blood-brain-barrier (BBB) with reasonable transendothelial electrical resistance (TEER) values of 30-100 $\Omega/cm^2$. Briefly, this cell model has been extensively characterized and found to maintain a brain endothelial phenotype; despite lower complexity due to lack of co-cultured astrocytes/pericytes or application of flow-based shear stress, hCMEC monolayers have suitable barrier characteristics with high junctional integrity, restricted permeability to paracellular tracers, and reasonable transendothelial electrical resistance (TEER) values of 30-100 $\Omega/cm^2$. The Transwell permeability assay was then performed based on a previously established assay using 24-well plates (Sigma-Aldrich) containing 6.5 mm Transwell inserts (0.4 µm pore polycarbonate membrane (Corning)) as follows:

hCMEC/D3 cells were grown in endothelial cell medium (ECM), containing EndoGro-MV complete media, 10% fetal bovine serum (FBS), 1% penicillin-streptamycine (P/S), and 1 ng/mL FGF-2 on the membranes of the Transwell inserts ($2 \times 10^5$ cells/insert) (37° C. and 5% $CO_2$) until full confluency was reached (normally after 5-7 days of culture). Confluency and BBB-type tightness was verified by TEER analysis; TEER values of 60-80 $\Omega cm^2$ were obtained. The upper and lower chambers then were reconstituted with 200 µl and 800 µl, respectively, of ECM containing 2% FBS. The N-terminal fluorescein-labeled 12 amino acid-long peptide THRPPMWSPVWP-amide (Fluos-Trfb) known to readily cross the BBB via binding to the transferrin receptor, was used as a positive control for BBB permeability in this model. Synthetic N-terminal fluorescein-labeled 2e (Fluos-2e) (10 µM), Fluos-Trfb (10 µM), or Lucifer yellow (20 µM) (control for BBB tightness) were added to the upper (donor) chamber of the Transwell device (n=3 for each incubation time point and reagent) and incubated (37° C., 5% $CO_2$) with the cells for the indicated time points.

For quantification of fluorescently labeled peptides present in the lower (acceptor) chamber, 100 μl of medium was transferred from the lower chamber to a well of a 96-well black polystyrene plate (Greiner) and fluorescence at 519 nm (excitation at 495 nm) was measured with a fluorescence microplate reader (Perkin Elmer Enspire). As a reference point for the maximum fluorescence intensity, 100 μl of medium from the upper chamber at 0 h was also transferred and quantified. Of note, fluorescence of Fluos-2e or Fluos-Trfb was directly proportional to their concentrations as determined by calibration curves. Lucifer yellow in the lower chamber was quantified by measuring the fluorescence at 530 nm (excitation at 485 nm). Relative permeability (FIG. 3f) was calculated by dividing the fluorescence value of the aliquot from the lower chamber at each time point by the fluorescence value of the 0 h-lower chamber aliquot.

Apparent permeability ($P_{app}$) at 2 h was calculated by the following equation:

$$P_{app} (cm/s) = (dQ/dt)(1/A)(1/C_0) \text{ (cm/s)}$$

where (dQ/dt) is the amount of peptides or Lucifer yellow present in the lower chamber at the 2 hour time point (nmol/s), A is the membrane area of the upper chamber (0.33 $cm^2$) and $C_0$ is their initial concentration in the upper chamber (nmol/ml). Reported $P_{app}$ values are means (±SEM) from at least 3 transport assays (each of them performed in triplicates).

Of note, studies on the transport rate of Lucifer yellow ($P_{app}$=5.3×10$^{-6}$ (±2.7) cm/s at 2 h) were performed in parallel to the studies on the peptide transport and were consistent with a good tightness or integrity of the hCMEC monolayer, confirming the TEER measurements. In addition, a $P_{app}$ of 20.8×10$^{-6}$ (+1.9) cm/s was found (at 2 h) for Fluos-Trfb, which further confirmed the validity of the results of the permeability assay.

Finally, to confirm the above results and the intact nature of the Fluos-2e molecule after crossing the hCMEC BBB-type cell layer, aliquots of upper and lower chambers were analysed by RP-HPLC and MALDI-TOF-MS (FIG. 4g). RP-HPLC (detection at λ=214 nm) was performed using a YMC basic column (length 250 mm; ID 4.6 mm; 5 μm particle size), flow rate 1.0 ml/min and eluting buffers A, 0.058% (v/v) TFA in water, and B, 0.05% (v/v) TFA in 90% (v/v) $CH_3CN$ in water. The elution gradient was 10-90% B in A over 30 min.

Example 2

Design of Peptides and Experiments

Macrocyclic Inhibitory peptides ("MCIPs") were designed using R3-GI (1), a partial sequence peptide of IAPP (residues 8-28 of IAPP), containing an RRR tripeptide instead of the three residues 19-21 of the IAPP sequence (see also FIG. 1), as a template, conformational restriction by cyclization, sequence truncation, specific N-methylations, and multiple amino acid substitutions with Gly or D-residues (FIG. 1). Notably, 1 of FIG. 1 is able to inhibit A40(42) but not IAPP amyloidogenesis.

As interaction surfaces mimicking surfaces of β-hairpins/β-sheet folds of IAPP are likely required for inhibitory function, the present inventors first asked whether cyclization of partially disordered 1 would affect its function and synthesized its cyclic analog is (FIG. 1). Amyloid formation of Aβ40 and IAPP alone or with is were followed by ThT binding assay and results confirmed by TEM (FIG. 2). In addition, aged solutions were added to cells and cell-damage studied by the 3-[4,5 dimethylthiazol-2-yl]-2,5-diphenyltetrazolium bromide (MTT) reduction assay in rat pheochromocytoma (PC12; Aβ40) or rat insulinoma (RIN5fm; IAPP) cells. 1a strongly suppressed amyloidogenesis and cell-damaging effects of Aβ40 (FIGS. 2a,b,e). Titrations of cytotoxic Aβ40 species with 1a yielded an $IC_{50}$ of 79.8 (+30.3) nM which was nearly identical to the $IC_{50}$ of 1 (Table 1). Moreover and in contrast to 1, 1a also strongly suppressed amyloid self-assembly and cell damage by IAPP; an $IC_{50}$ of 126 (+39.1) nM was determined (FIGS. 2c,d,e; Table 1). The cyclic constraint of 1a is thus fully compatible with potent amyloid inhibitory function toward both Aβ40 and IAPP.

TABLE 1

| | $IC_{50}$ of inhibitory effects on cell-damaging amyloid self-assembly of Aβ40 or IAPP. | |
|---|---|---|
| Peptide | $IC_{50}$ (±SD) (nM) Aβ40 inhibition[a] | $IC_{50}$ (±SD) (nM) IAPP inhibition[a] |
| R3-GI (1) | 116 (±11)[5] | n.d.[b] |
| 1a | 79.8 (±30.3) | 126 (±39.1) |
| 2 | n.d.[b] | n.d.[b] |
| 2a | 125.1 (±73.4) | 47.6 (±15.5) |
| 2b | 654.3 (±227.8) | 425.7 (±77.7) |
| 2c | 204 (±83.6) | n.d.[b] |
| 2d | 702.6 (±339.3) | n.d.[b] |
| 2e | 542.5 (±240.7) | n.d.[b] |

[a] $IC_{50}$s, means (±SD) from 3-4 titration assays (n = 3 each) (Aβ40, 500 nM; IAPP, 100 nM).
[b] n.d., non-determined (non-inhibitor).

To reduce the size of 1, the inventors synthesized its analog 2 lacking region IAPP(8-13). N-terminal truncation was based on the suggestion that IAPP(14-18) and IAPP(22-28) mediate key interactions for both IAPP self- and hetero-assembly. However, 2 was unable to block amyloid self-assembly of the two polypeptides (FIGS. 2a-d).

The inventors hypothesized that conformational restriction of 2 via cyclization might restore inhibitory function and synthesized 2a with two flanking disulfide-bridged cysteines (FIG. 1). In fact, 2a blocked Aβ40 cytotoxic self-assembly with an $IC_{50}$ of 125.1 (+73.4) nM which is close to the $IC_{50}$ of 1 (FIGS. 2a,b,e; Table 1). Moreover, 2a blocked IAPP cytotoxic self-assembly as well; an $IC_{50}$ of 47.6 (±15.5) nM was determined consistent with 2a being even more potent (~3-fold) than the longer is (FIGS. 2c,d,e, Table 1). Interestingly, the far-UV CD spectra of both cyclic and linear peptides had similar shapes and were indicative of random coil and β-sheet/β-turn contents at ~1/1 ratio (FIG. 2f). Differences between inhibitory activities might thus be due to stabilization of specific folds enabling specific side chain topologies and high affinity functional interactions with Aβ40 or IAPP. Indeed, fluorescence spectroscopic titrations revealed mid-nanomolar app. $K_d$s for interactions of cyclic inhibitors is and 2a with N-terminal fluorescently labeled Aβ40 or IAPP as previously found for 1, whereas much weaker binding was found for the non-inhibitor 2.

Recent findings suggest that IAPP residues Phe15, Leu16, Phe23 and Ile26 are key residues of IAPP-IAPP and IAPP-Aβ40(42) interactions and that the nature of the linker tripeptide determines ISM function. Aiming at minimizing IAPP-derived elements, the inventors next asked if these 4 residues and the RRR linker would be sufficient for amyloid inhibitory function and synthesized analog 2b with 7 out of the ii non-Gly residues of 2a substituted with Gly (except for Cys); only the side chains of the above 4 residues were maintained (FIG. 1).

Remarkably, 2b strongly suppressed amyloid self-assembly and cell-damaging effects of both Aβ40 ($IC_{50}$, 654.3 (±227.8) nM) and IAPP ($IC_{50}$, 425.7 (+77.7) nM) (FIG. 3, Table 1). Such suppressive effect was not, or to a much lesser degree, seen for mutant peptides in which one or several of residues F15, L16, F23 and I26 had been replaced by Ala (data not shown). In addition, fluorescence spectroscopic titrations yielded mid-nanomolar app. $K_d$s for the interactions of 2b with fluorescently labeled Aβ40 and IAPP which were in a similar range to the $IC_{50}$s (data not shown). The CD spectrum of 2b exhibited one major minimum at 230 nm, which was indicative of stabilized turn structures (FIG. 3f). The 4 IAPP key residues and the RRR tripeptide arranged within the cyclic oligoglycine scaffold of 2b may thus comprise a motif media-ting cross-amyloid inhibitor function; moreover, the potent inhibitory effects of 2b toward amyloid self-assembly of both Aβ40 and IAPP make it a lead for anti-amyloid drugs.

Resistance toward plasma proteases is an important requirement for any drug candidate. Therefore, the inventors determined the proteolytic stabilities of the above peptides in human plasma in vitro using RP-HPLC and MALDI-TOF-MS. Unfortunately, all of them were rapidly degraded; half-life times (to) were <1 h (FIG. 4a).

To improve the proteolytic stability of 2b, 3 rounds of sequence optimization were performed next (FIG. 1). First, analog 2c with 3 D-Arg in the linker region instead 3 L-Arg was synthesized followed by 2d in which, in addition, Phe and Leu residues were replaced by D-ones. However, to values were only slightly improved (~1-2 h) (FIG. 4a). Thus, 2e in which additionally the two L-Cys were replaced by D-Cys was synthesized. Most importantly, 2e exhibited highly improved proteolytic stability also in comparison to other peptides (to >11 h) being >30-fold more resistant than 1 ($t_{1/2}$~20 min) and >15-fold more resistant than its L-precursor 2b ($t_{1/2}$~45 min) (FIG. 4a).

The inventors next asked whether switching chiralities may have affected 2b structure and function. In fact, the shapes of the CD spectra of 2c-2e were similar to 2b but their minima were blue-shifted indicative of different types of turns and/or β-strand contents (data not shown). However, 2c, 2d, and 2e bound both Aβ40 and IAPP with similar high affinities to 2b (data not shown). Notably, all three peptides were nanomolar inhibitors of Aβ40 amyloid self-assembly; their $IC_{50}$ values were similar to the $IC_{50}$ of 2b (FIGS. 3a-e, Table 1). Most remarkably, all of them lost the ability of 2b to block IAPP amyloidogenesis, which rendered them into Aβ40-selective inhibitors; notably, 2e selectivity was maintained for up to an at least 50-fold molar excess to IAPP (FIGS. 3c,d,e).

Next, the inventors studied effects of MCIPs on Aβ42 amyloidogenesis. In fact, all of them strongly suppressed formation Aβ42 fibrils and cell-damaging assemblies (FIGS. 4b,c). Titrations of N-terminal fluorescently labeled Aβ42 (FITC-Aβ42) (5 nM) with MCIPs revealed mid-to-low nanomolar binding affinities (data not shown). Most importantly, ex vivo electrophysiological studies in mouse brains showed that 2a, 2b and 2e ameliorated Aβ42-mediated inhibition of hippocampal synaptic long term potentiation (LTP) which is linked to loss of memory and cognitive functions in AD; these results support the physiological relevance of the in vitro results (FIGS. 4d,e).

Blood-brain-barrier (BBB) crossing is a highly desirable property for drug candidates targeting the amyloid cascade in AD. However, the highly restrictive nature of the BBB allows for only very few neuropharmaceuticals to be delivered to the brain. MCIP 2e is a quite small (<2 kDa) macrocyclic peptide containing an RRR segment, two amide bond N-methylated residues, 4 aromatic/large hydrophobic residues, and 8 flexible Gly residues; these are all features linked to membrane permeability. Thus, the inventors next studied whether N-terminal fluorescein-labeled 2e (Fluos-2e) can cross the BBB by using a well-established cell model of human cerebral microvascular endothelial cells (hCMECs) grown as confluent monolayers on Transwell membranes. In fact, Fluos-2e crossed the monolayer with an apparent permeability ($P_{app}$) at 2 h of $14.6 \times 10^{-6}$ (±3.36) cm/s (mean (±SEM), n=3), which is similar to the $P_{app}$ of other BBB crossing peptides (FIGS. 4f,g). Of note, hCMECs express substantial surface levels of the prominent brain protease neprilysin and 2e was fully resistant to degradation in an in vitro human neprilysin digestion assay (data not shown).

The present inventors were thus able to design and produce highly potent amyloid inhibitors of both Aβ40(42) and IAPP, or of Aβ40(42) alone. They also showed that the chirality of these inhibitors controls inhibitor selectivity. Furthermore, a systematic sequence optimization led to inhibitor 2e, which is a nanomolar Aβ40(42)-selective inhibitor which exhibits high proteolytic stability in human plasma and human blood-brain-barrier crossing ability in a cell model which are two highly desirable properties for anti-amyloid drugs in Alzheimer's disease.

The invention claimed is:

1. A peptide having an amino acid sequence according to formula 0

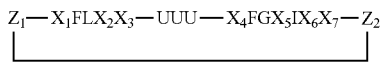

(Formula 0)

wherein

Z1 and Z2 are selected from the following pairs
a) cysteine and cysteine,
b) aspartic acid and lysine, or lysine and aspartic acid,
c) aspartic acid and ornithine, or ornithine and aspartic acid,
d) aspartic acid and 2,4-diaminobutyric acid, or 2,4-diaminobutyric acid and aspartic acid,
e) aspartic acid and 2,3-diaminopropionic acid, or 2,3-diaminopropionic acid and aspartic acid,
f) glutamic acid and lysine, or lysine and glutamic acid,
g) glutamic acid and ornithine, or ornithine and glutamic acid,
h) glutamic acid and 2,4-diaminobutyric acid, or 2,4-diaminobutyric acid and glutamic acid,
i) glutamic acid and 2,3-diaminopropionic acid, or 2,3-diaminopropionic acid and glutamic acid;
with ⌊⌋ denoting a covalent bond between Z1 and Z2, thus providing for a cyclization of the peptide;

X1, X2, X3, X4, X5, X6, and X7 are, independently at each occurrence, selected from glycine, asparagine, valine, histidine, leucine, serine, alanine, and threonine;
F is, independently at each occurrence, phenylalanine;
L is leucine;
U is, independently at each occurrence, selected from arginine, homoarginine, citrulline, ornithine, lysine, and norleucine;
G is glycine;
I is isoleucine;
wherein Z1, Z2, X1-X7, F, L, U, G and I are L-amino acid residues or D-amino acid residues, or some of Z1, Z2, X1-X7, F, L, U, G and I are L-amino acid residues and others are D-Amino acid residues;
and pharmaceutically acceptable salts, esters, solvates, polymorphs and modified forms thereof.

2. The peptide according to claim 1, having an amino acid sequence according to formula 1

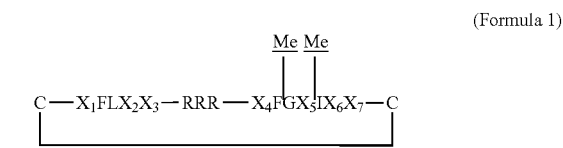

(Formula 1)

or an amino acid sequence according to formula 1*

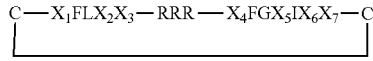

(Formula 1*)

wherein
C is cysteine;
X1, X2, X3, X4, X5, X6, and X7 are, independently at each occurrence, selected from glycine, asparagine, valine, histidine, leucine, serine, alanine, and threonine;
F is, independently at each occurrence, phenylalanine;
L is leucine;
R is arginine;
G is glycine;
I is isoleucine; ⌊⌋ is a disulfide bond;

is N-methyl;
wherein C, X1-X7, F, L, R, G and I are L-amino acid residues or D-amino acid residues, or some of C, X1-X7, F, L, R, G and I are L-amino acid residues and others are D-amino acid residues;
and pharmaceutically acceptable salts, esters, solvates, polymorphs and modified forms thereof.

3. The peptide according to claim 1, wherein either
a) X1 and X4 are asparagine, X2 is valine, X3 is histidine, X4 is glycine, X5 is glycine, X6 and X7 are glycine;

b) X1-X7 are glycine, alanine or serine;
c) X1-X7 are glycine;
d) X1-X3 are glycine, X4 is asparagine, X5 is alanine, X6-X7 are glycine; or
e) X1-X3 are glycine, X4 is asparagine, X5 is alanine, X6 is leucine, X7 is serine.

4. The peptide according to claim 1,
wherein Z1, Z2, C, X1-X7, F, L, U, R, G, and I are L-amino acid residues.

5. The peptide according to claim 1,
wherein R is, at each occurrence, D-arginine, and/or
wherein F is, at each occurrence, D-phenylalanine, and/or
wherein L is D-leucine, and/or
wherein Z1, Z2 and C are D-amino acid residues, and/or
wherein I is D-isoleucine or N-methyl-D-isoleucine.

6. The peptide according to claim 1, having a sequence according to a formula selected from the following formulae 2a-2e, and 2a*-2e*:

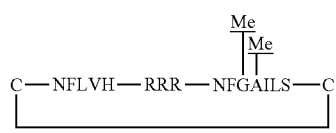
(Formula 2a)

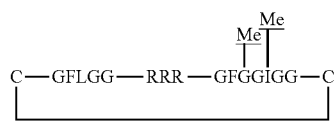
(Formula 2b)

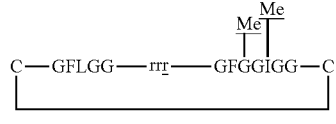
(Formula 2c)

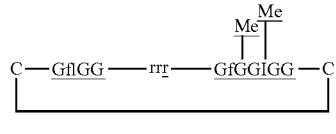
(Formula 2d)

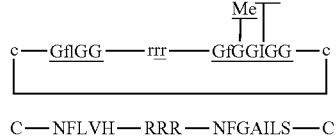
(Formula 2e)

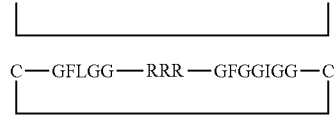
(Formula 2a*)

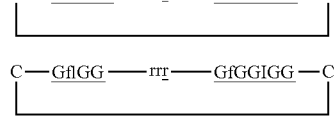
(Formula 2b*)

(Formula 2c*)

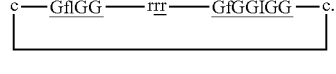
(Formula 2d*)

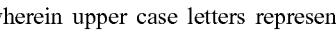
(Formula 2e*)

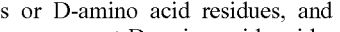

wherein upper case letters represent L-amino acid residues or D-amino acid residues, and wherein lower case letters represent D-amino acid residues.

7. The peptide according to claim 6, having a sequence according to a formula selected from 2e and 2e*

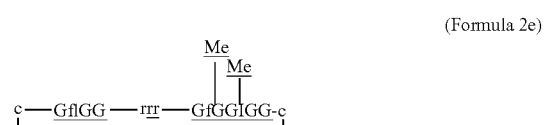
(Formula 2e)

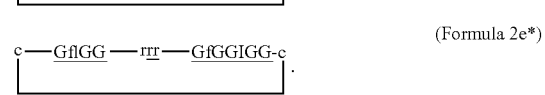
(Formula 2e*)

8. The peptide according to claim 1, wherein said peptide consists of a sequence according to any of formulae 0, 0a, 1, 1*, 2a-2e, and 2a*-2e*:

$$Z_1 - X_1FLX_2X_3 - UUU - X_4FGX_5IX_6X_7 - Z_2$$
(Formula 0)

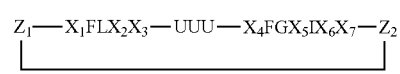
(Formula 0a)

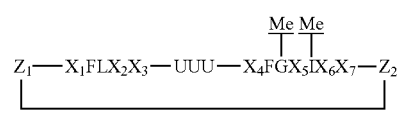
(Formula 1)

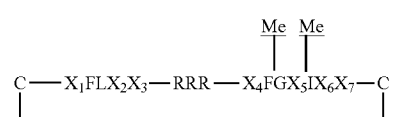
(Formula 1*)

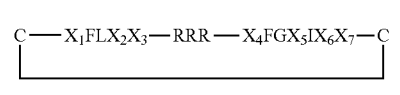
(Formula 2a)

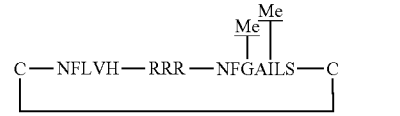
(Formula 2b)

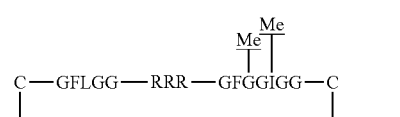
(Formula 2c)

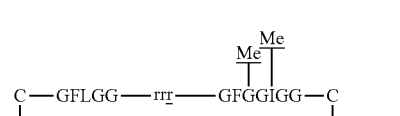
(Formula 2d)

(Formula 2e)

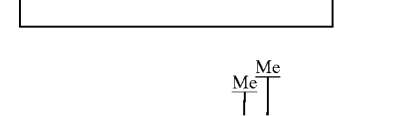
(Formula 2a*)

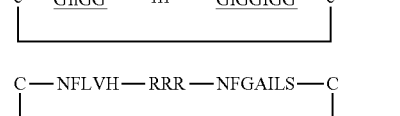

-continued

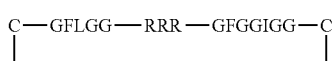 (Formula 2b*)

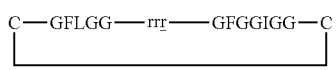 (Formula 2c*)

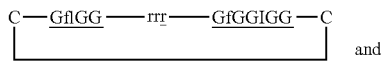 (Formula 2d*)

and

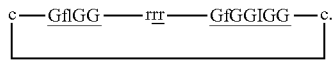 (Formula 2e*).

9. The peptide according to claim 1, wherein said peptide is an amyloid inhibitory peptide that binds to Aβ40(42) and/or to islet amyloid polypeptide (IAPP).

10. A pharmaceutical composition comprising a peptide according to claim 1 and a pharmaceutically acceptable excipient.

11. A kit for the in-vitro or in-vivo detection of amyloid fibrils or aggregates, or for the diagnosis of Alzheimer's disease or type 2 diabetes in a patient, said kit comprising the peptide according to claim 1, in a freeze-dried form in a suitable container, a buffered solvent in a separate container for reconstitution of said peptide in solution, and, optionally, means to dispense said peptide once reconstituted in solution.

12. The peptide, according to claim 1, wherein said peptide has an amino acid sequence according to formula 0a

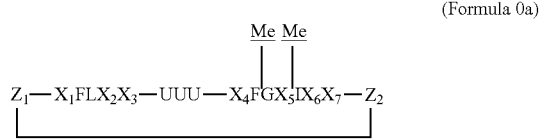 (Formula 0a)

wherein
Z1, Z2, X1-X7, F, L, U, G, I are as defined in claim 1, and

is N-methyl.

13. The peptide according to claim 6, wherein upper case letters represent L-amino acid residues and lower case letters represent D-amino acid residues.

14. The peptide according to claim 7, wherein upper case letters represent L-amino acid residues and lower case letters represent D-amino acid residues.

\* \* \* \* \*

UNITED STATES PATENT AND TRADEMARK OFFICE
CERTIFICATE OF CORRECTION

PATENT NO. : 11,498,943 B2
APPLICATION NO. : 17/048870
DATED : November 15, 2022
INVENTOR(S) : Aphrodite Kapurniotu et al.

It is certified that error appears in the above-identified patent and that said Letters Patent is hereby corrected as shown below:

In the Specification

Column 2,
Line 2, "f) glutamic acid" "f)" starts on a new line

Column 8,
Line 13, "it also possible" should read --it is also possible--
Line 63, "effects of effects of" should read --effects of--

Column 9,
Line 8, "with is and" should read --with 1a and--
Line 9, "(bars wo nm)." should read --(bars 100 nm).--
Line 16, "MIT reduction" should read --MTT reduction--
Line 20, "by MIT" should read --by MTT--
Line 34, "by MIT" should read --by MTT--

Column 11,
Line 27, "MIT assay" should read --MTT assay--
Line 42, "MIT" should read --MTT--
Line 47, "the MIT" should read --the MTT--

Column 12,
Line 24, "pH 7.4 (i %" should read --pH 7.4 (1%--
Line 33, "KdDs are" should read --Kds are--

Column 14,
Line 2, "(2-3 MO" should read --(2-3 Mµ)--

Column 16,
Line 1, "with is were" should read --with 1a were--

Signed and Sealed this
Sixth Day of June, 2023

Katherine Kelly Vidal
*Director of the United States Patent and Trademark Office*

Line 10, "(+30.3)" should read --(±30.3)--
Line 13, "(+39.1)" should read --(±39.1)--
Line 48, "(+73.4)" should read --(±73.4)--
Line 52, "longer is" should read --longer 1a--
Line 61, "inhibitors is" should read --inhibitors 1a--

Column 17,
Lines 3-4, "out of the ii" should read --out of the 11--
Line 9, "(+77.7)" should read --(±77.7)--
Line 30, "times (to)" should read --times ($t_{1/2}$)--
Line 40, "(to >11h)" should read --($t_{1/2}$ >11h)--